(12) United States Patent
Frinking

(10) Patent No.: US 9,734,584 B2
(45) Date of Patent: Aug. 15, 2017

(54) SEGMENTATION IN DIAGNOSTIC IMAGING APPLICATIONS BASED ON STATISTICAL ANALYSIS OVER TIME

(71) Applicant: BRACCO SUISSE SA, Manno (CH)

(72) Inventor: Peter Frinking, Geneva (CH)

(73) Assignee: Bracco Suisse SA, Manno (CH)

( * ) Notice: Subject to any disclaimer, the term of this patent is extended or adjusted under 35 U.S.C. 154(b) by 91 days.

(21) Appl. No.: 14/654,449

(22) PCT Filed: Dec. 18, 2013

(86) PCT No.: PCT/EP2013/077152
§ 371 (c)(1),
(2) Date: Jun. 19, 2015

(87) PCT Pub. No.: WO2014/096041
PCT Pub. Date: Jun. 26, 2014

(65) Prior Publication Data
US 2015/0348277 A1    Dec. 3, 2015

(30) Foreign Application Priority Data

Dec. 21, 2012   (EP) .................................. 12199175

(51) Int. Cl.
G06K 9/00         (2006.01)
G06T 7/00         (2017.01)
(Continued)

(52) U.S. Cl.
CPC ............ *G06T 7/0097* (2013.01); *A61B 8/481* (2013.01); *A61M 5/007* (2013.01); *G06T 7/0014* (2013.01);
(Continued)

(58) Field of Classification Search
None
See application file for complete search history.

(56) References Cited

FOREIGN PATENT DOCUMENTS

| CN | 101917908 | 12/2010 |
|---|---|---|
| CN | 102460506 | 5/2012 |

(Continued)

OTHER PUBLICATIONS

Rafter, Patrick et al., "Imaging technologies and techniques," Cardiology Clinics vol. 22, pp. 181-197, 2004.
International Search Report for International Application No. PCT/EP2013/077152, European Patent Office, Rijswijk, NL, Mar. 25, 2014.
(Continued)

*Primary Examiner* — Atiba O Fitzpatrick
(74) *Attorney, Agent, or Firm* — Fogg & Powers LLC

(57) ABSTRACT

An embodiment of a segmentation solution for use in diagnostic imaging applications is proposed. A corresponding embodiment of a data-processing segmentation method comprises: providing a representation over a non-zero analysis time period of a body-part being perfused with a contrast agent, the representation comprising, for each location of a set of locations of the body-part, an indication of a response over the analysis time period of the location to an interrogation signal; calculating, for each selected location of a set of selected locations, the value of at least one statistical parameter of a statistical distribution of the response over the analysis time period of the selected location, the set of selected locations comprising all the locations or a part thereof; and segmenting the selected locations according to a comparison between the values of said at least one statistical parameter for the selected locations with at least one segmentation threshold.

32 Claims, 14 Drawing Sheets

(51) Int. Cl.
*A61M 5/00* (2006.01)
*A61B 8/08* (2006.01)
*G06T 7/174* (2017.01)

(52) U.S. Cl.
CPC .... *G06T 7/174* (2017.01); *G06T 2207/10132* (2013.01); *G06T 2207/20112* (2013.01); *G06T 2207/30004* (2013.01)

(56) References Cited

FOREIGN PATENT DOCUMENTS

| | | |
|---|---|---|
| CN | 102483847 | 5/2012 |
| EP | 0458745 | 11/1991 |
| EP | 0554213 | 8/1993 |
| WO | 9115244 | 4/1991 |
| WO | 9409829 | 10/1993 |
| WO | 9516467 | 12/1994 |
| WO | 2004110279 | 12/2004 |
| WO | 2006018433 | 2/2006 |
| WO | 2011026866 | 3/2011 |

OTHER PUBLICATIONS

J. Zhang, W. Hu, Y. Wu, D. Klemer, A. Hall, C. Kahn, "A Novel Model for Contrast Enhanced Ultrasound Video and Its Applications", 2006 IEEE Ultrasonics Symposium, pp. 1726-1729.

Pochon Sibylle, Tardy Isabelle, Bussat Philippe; Bettinger Thierry; Brochot Jean; von Wronski Mathew; Passantino Lisa; Schneider Miche; "BR55: A Lipopeptide-Based VEGFR2-Targeted Ultrasound Contrast Agent for Molecular Imaging of Angiogenesis", Investigative Radiology: Feb. 2010—vol. 45—Issue 2—pp. 89-95.

European Patent Office, "Office Action from EP Application No. 13814107.2 mailed Apr. 20, 2016", "from Foreign Counterpart of U.S. Appl. No. 14/654,449", Apr. 20, 2016, pp. 15, Published in: EP.

Isabelle Tardy, Sibylle Pochon, Martine Theraulaz, Patricia Emmel, Lisa Passantino, Francois Tranquart, Michel Schneider, Ultrasound molecular imaging of VEGFR2 in a rat prostate tumor model using BR55, Investigative Radiology; vol. 45, No. 10, Oct. 2010; 573-578.

State Intellectual Property Office of the People's Republic of China, "Notification of the First Office Action for CN Application No. 201380066958.4", "Foreign Counterpart to U.S. Appl. No. 14/654,449", Mar. 31, 2017, pp. 1-23, Published in: CN.

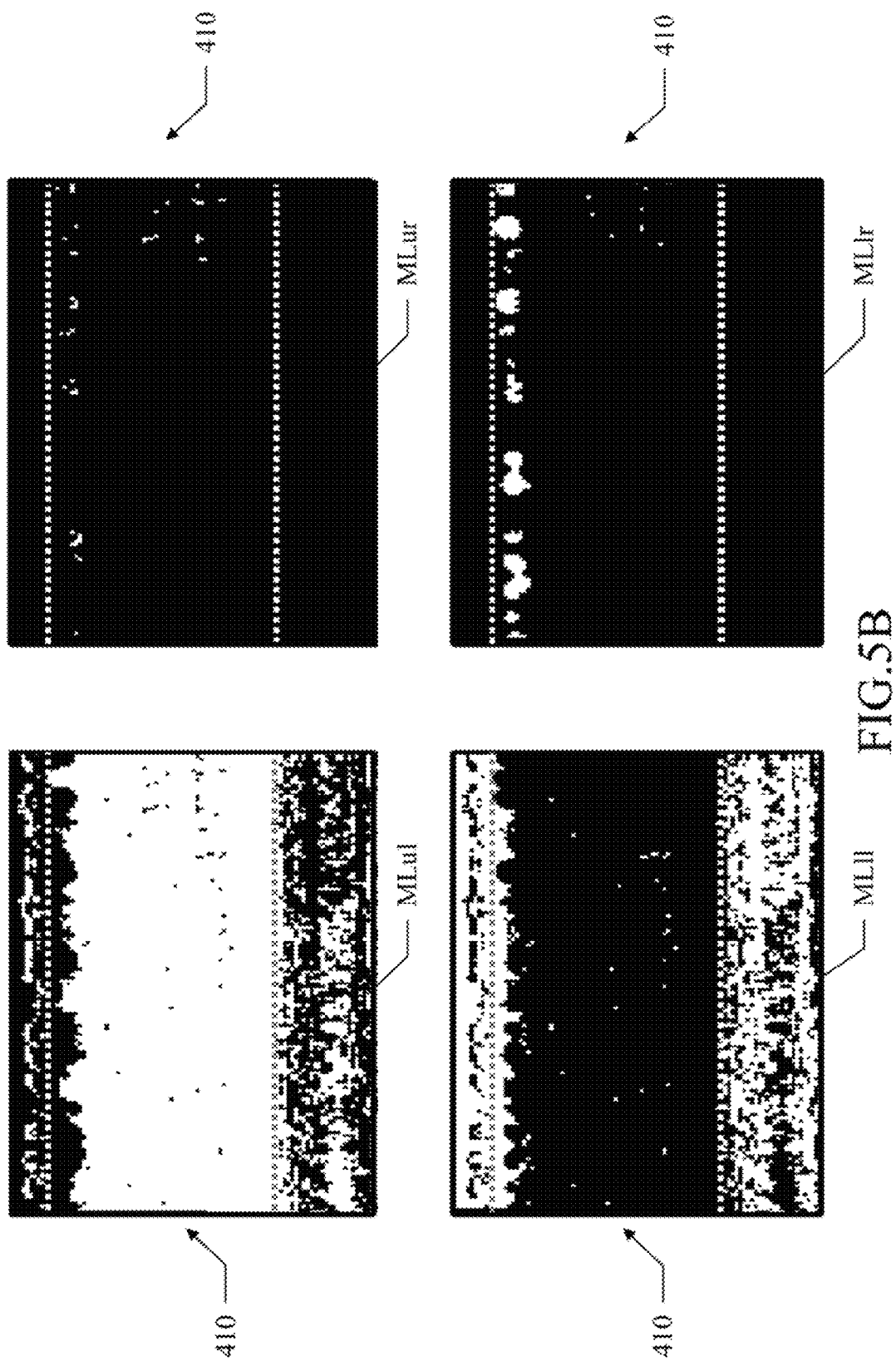

SEGMENTATION IN DIAGNOSTIC IMAGING APPLICATIONS BASED ON STATISTICAL ANALYSIS OVER TIME

PRIORITY CLAIM

The present application is a national phase application filed pursuant to 35 USC §371 of International Patent Application Serial No. PCT/EP2013/077152, filed Dec. 18, 2013; which further claims the benefit of European Patent Application 12199175.6, filed Dec. 21, 2012; all of the foregoing applications are incorporated herein by reference in their entireties.

TECHNICAL FIELD

The solution according to the present disclosure relates to the diagnostic imaging field. More specifically, this solution relates to segmentation in diagnostic imaging applications.

BACKGROUND

Segmentation techniques are widely used in diagnostic imaging applications (or simply imaging applications); generally speaking, any segmentation technique is aimed at segmenting a representation of a body-part of a patient under analysis (for example, a digital image thereof) into two or more segments, each one comprising a portion of the representation of the body-part with substantially homogenous characteristics.

For example, segmentation techniques may be used for the assessment of blood perfusion in Dynamic Contrast-Enhanced Ultrasound (DCE-US) imaging applications. In this case, an ultrasound contrast agent (UCA), or simply contrast agent, acting as an efficient ultrasound reflector, is administered to the patient. The contrast agent flows at the same velocity as red-blood cells in the patient, so that its detection by recording echo signals that are returned in response to ultrasound waves provides information about the corresponding blood perfusion. Particularly, for each location of the body-part wherein the echo signal has been recorded, the value of a perfusion parameter that characterizes it (such as a peak enhancement) is calculated (for example, from a parametric function fitting the echo signal over time). A parametric image is built by assigning, to each pixel representing a location of the body-part, the corresponding perfusion parameter value. The parametric image may be used to calculate a consolidated value of the perfusion parameter values (for example, their mean value) in an analysis region of the body-part comprising a lesion; typically, the consolidated value of the analysis region is expressed in relative terms with respect to the consolidated value of the perfusion parameter values in a control region of the body-part comprising healthy tissue. This relative consolidated value provides a quantitative characterization of the lesion, which may be used, for example, in its therapeutic follow-up.

However, the consolidated values of the analysis region and of the control region are intrinsically affected by a certain degree of inaccuracy, since they are calculated globally in regions of the body-part that are not perfectly homogenous; for example, the analysis region may comprise necrotic tissues that are hypo-perfused and the control region may comprise big blood vessels that are hyper-perfused. These hypo-perfused and hyper-perfused portions of the analysis region and of the control region, respectively, cause errors in their consolidated values that reflect in the relative consolidated value of the analysis region. This drawback is particularly acute in the therapeutic follow-up, wherein even subtle changes in the perfusion of the lesion during its treatment may be indicative of the effectiveness of the treatment.

Alternatively, WO-A-2011/026866 (the entire disclosure of which is herein incorporated by reference) discloses determining an analysis function for each pixel of an analysis area (defining a region of interest) by fitting its echo-power signal by a model function of time (for example, a lognormal distribution function), and determining a reference function for a reference area (including healthy parenchyma) by fitting an average of its echo-power signals by the same model function of time. For each pixel of the analysis area, a difference function is calculated by subtracting the reference function from its analysis function; the pixel is then assigned to different classes according to a polarity trend of its difference function (i.e., positive unipolar class, negative unipolar class, positive-to-negative bipolar class, and negative-to-positive bipolar class). For this purpose, it is possible to calculate a positive energy and a negative energy of the difference function; when the sum of the positive energy and the negative energy is higher than a significance threshold, a relative positive energy and a relative negative energy are calculated. If the relative positive energy or the negative relative energy exceeds a discrimination threshold, the difference function is assigned to the positive unipolar class or to the negative unipolar class, respectively; conversely, the difference function is assigned to the positive-to-negative bipolar class or to the negative-to-positive bipolar class according to an order of its main change of polarity.

Segmentation techniques may also be used in Ultrasound Molecular Imaging (UMI) applications. In this case, a target-specific contrast agent is used; the target-specific contrast agent is adapted to reach a specific biological target (for example, a lesion), and then remain immobilized thereon by means of a specific interaction. The detection of any particles of the target-specific contrast agent that are immobilized in the body-part allows identifying the corresponding lesion that would otherwise be difficult to discover; moreover, the quantification of these immobilized particles allows determining a status of the lesion, which may be used, for example, in its therapeutic follow-up.

However, the detection and the quantification of the immobilized particles of the target-specific contrast agent is hindered by the fact that only a small fraction of the total amount thereof actually reaches the target and remains immobilized thereon; most of the target-specific contrast agent continues instead to circulate for quite a long time (such as, several minutes)—for example, until it is filtered out by the lungs and/or in the liver of the patient. Therefore, the particles of the target-specific contrast agent in the body-part comprise both a contribution of the particles that are immobilized thereon and a contribution of the particles that are still circulating; as a consequence, it is quite difficult to discriminate between the two contributions (especially at early times after the administration of the target-specific contrast agent).

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of basing the segmentation on a statistical analysis over time.

Particularly, an aspect provides a data-processing segmentation method for use in diagnostic imaging applications, wherein selected locations of a representation of a body-part being perfused with a contrast agent are segmented according to the values of at least one statistical parameter relating to a response to an interrogation signal over an analysis period of each selected location.

A further aspect provides a corresponding computer program.

A further aspect provides a corresponding computer program product.

A further aspect provides a corresponding system.

A further aspect provides a corresponding diagnostic imaging method.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution according to one or more embodiments of the present disclosure, as well as further features and the advantages thereof, will be best understood with reference to the following detailed description, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes such as value, content and representation). Particularly:

FIG. 5A-FIG. 5C show an example of application of the solution according to a further embodiment of the present disclosure.

DETAILED DESCRIPTION

Figure 1:
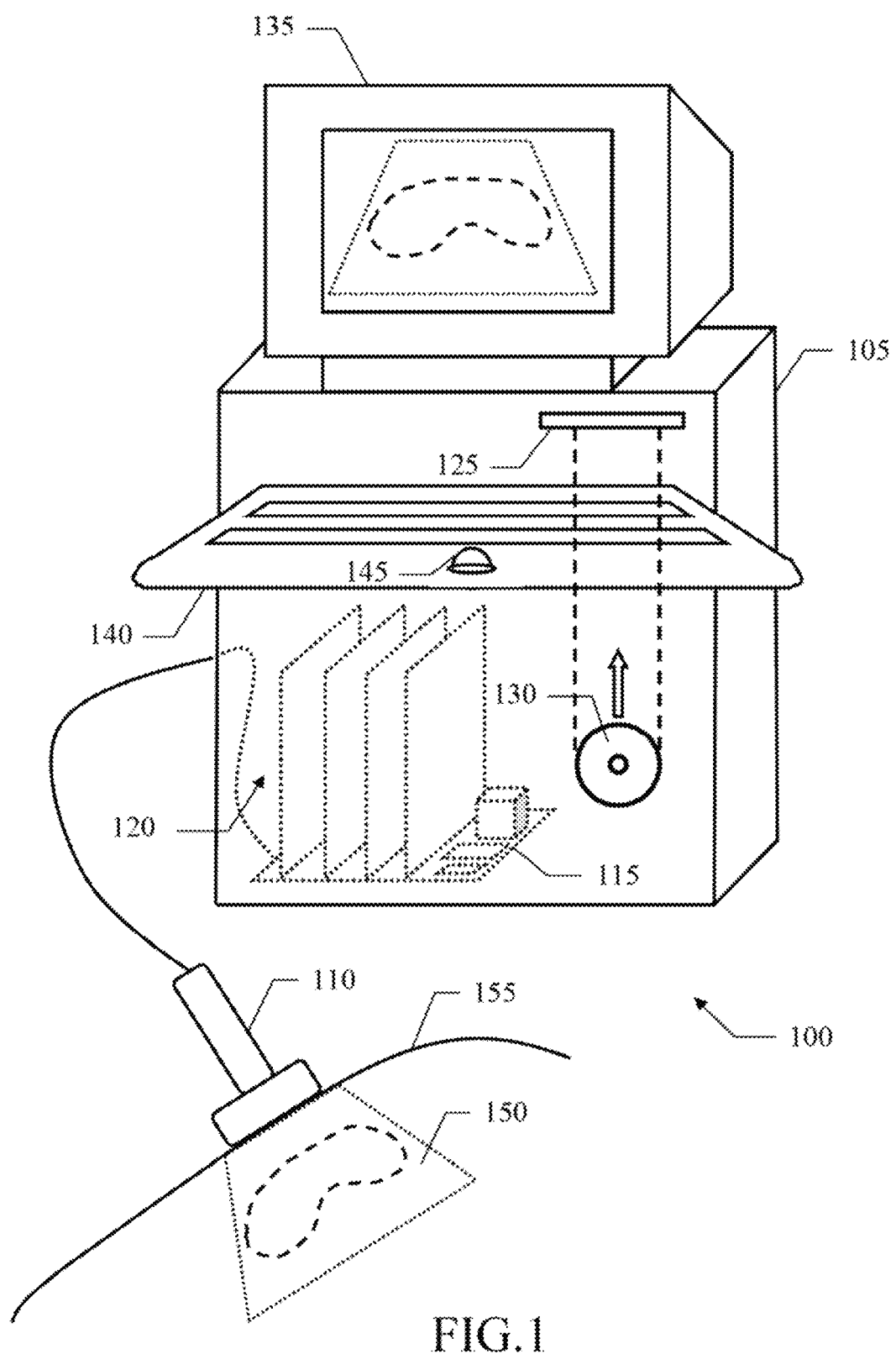
FIG. 1 shows a pictorial representation of a system that may be used to practice the solution according to an embodiment of the present disclosure.

With reference in particular to the FIG. 1, a system 100 is shown that may be used to practice the solution according to an embodiment of the present disclosure. Particularly, the system 100 is an ultrasound scanner, which comprises a central unit 105 and a hand-held transmit-receive imaging probe (or simply imaging probe) 110 connected thereto—for example, of the array type. The imaging probe 110 transmits ultrasound waves comprising a sequence of ultrasound pulses (for example, having a center frequency between 1 and 50 MHz), and receives radio-frequency (RF) echo signals resulting from the reflection of the ultrasound pulses in a selected scanning plane; for this purpose, the imaging probe 110 is provided with a transmit/receive multiplexer, which allows using the imaging probe 110 in the above-described pulse-echo mode.

The central unit 105 houses a motherboard 115, on which the electronic circuits controlling operation of the ultrasound scanner 100 are mounted (for example, a microprocessor, a working memory and a hard disk drive). Moreover, one or more daughter boards (denoted as a whole with the reference 120) are plugged into the motherboard 115; the daughter boards 120 provide the electronic circuits for driving the imaging probe 110 and for processing the echo signals. The central unit 105 is also equipped with a drive 125 for removable disks 130 (such as CDs or DVDs). A monitor 135 is connected to the central unit 105 for displaying images relating to an analysis process that is in progress. Operation of the ultrasound scanner 100 is controlled by means of a keyboard 140 (connected to the central unit 105 in a conventional manner); preferably, the keyboard 140 is provided with a trackball 145 that is used to manipulate the position of a pointer (not shown in the figure) on the monitor 135.

The ultrasound scanner 100 is used to analyze a body-part 150 of a patient 155; for this purpose, an (ultrasound) contrast agent is administered to the patient 155.

The contrast agent comprises particles acting as good ultrasound reflector. For example, the contrast agent is a suspension of gas-filled bubbles in a liquid carrier; typically, the gas-filled bubbles have diameters of the order of 0.1-5 µm, so as to allow their retaining within the vascular system of the patient 155, but at the same time to allow their passage through his/her capillaries. The gas-filled bubbles are generally stabilized by entraining or encapsulating the gas or a precursor thereof into a variety of systems, comprising phospholipids, emulsifiers, oils, thickeners, sugars, proteins or polymers; stabilized gas-filled bubbles are generally referred to as microvesicles. Particularly, microvesicles dispersed in an aqueous medium and bound at the gas/liquid interface by a very thin envelope involving a surfactant (i.e., an amphiphilic material) are also known as microbubbles. Alternatively, microvesicles surrounded by a solid material envelope formed by lipids or (natural or synthetic) polymers, are also known as microballoons or microcapsules. Another kind of contrast agent comprises a suspension of porous microparticles of polymers or other solids, which carry bubbles of gas entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial contrast agent comprising microvesicles is SonoVue by Bracco International BV (trademarks).

The contrast agent may also be of the target-specific type. A target-specific contrast agent is substantially free to circulate within the patient 155; however, the target-specific contrast agent is also capable of being immobilized on a selected (biological) target, so as to remain in a substantially fixed position for a certain period. For this purpose, the target-specific contrast agent is formulated in such a way as to bind selectively to the desired target by means of a specific interaction therewith. For example, this behavior may be achieved by incorporating a target-specific ligand capable of selectively binding (for example, through biochemical affinity and/or electrostatic interaction) to a desired tissue or receptor. Examples of target-specific ligands (which may be inserted into a membrane of the microbubbles) are monoclonal antibodies, peptides, or polysaccharides. The term tissue comprises (within its meaning) individual cells as well as aggregates of cells, such as membranes or organs. The term refers to either normal (healthy) or abnormal (pathological) cells or aggregates of cells. Examples of tissue are myocardial tissue (comprising myocardial cells and cardiomyocytes), membranous tissue (such as endothelium and epithelium), and connective tissue; examples of pathological tissue are infarcted heart tissue, blood clots, atherosclerotic plaques, inflammatory tissue and tumoral tissue. The receptors comprise any molecular structure located on the tissue (for example, within the cells or on their surfaces), which is capable to selectively bind to a specific substance. Exemplary receptors are glycoprotein GPIIbIIIa or fibrin (for example, located in blood clots or thrombi), P-Selectin (for example, located on activated endothelium of inflamed tissue) or KDR (for example, located in tumoral tissue). Examples of suitable target-specific contrast agents and of target-specific ligands are described in "Pochon et al., BR55: A lipopeptide-based VEGFR2-targeted ultrasound contrast agent for molecular imaging of angiogenesis. Inves Radiol 2010; 45:89-95" and "Tardy et al., Ultrasound molecular imaging of VEGFR2 in a rat prostate tumor model using BR55, Inves Radiol 2010; 45:573-578", and in WO-A-2006018433 (the entire disclosures of which are herein incorporated by reference).

The contrast agent may be detected by applying ultrasound waves and recording the echo signals that are returned in response thereto; since the contrast agent flows at the same velocity as red-blood cells in the patient 155, its detection and tracking in the body-part 150 provides information about the corresponding blood perfusion.

For example, the contrast agent is administered to the patient 155 intravenously as a bolus—i.e., a single dose provided by hand with a syringe over a short period of time (of the order of 2-20 seconds). The contrast agent circulates within the vascular system of the patient 155, so as to perfuse the body-part 150. At the same time, the imaging probe 110 is placed in contact with the skin of the patient 155 in the area of the body-part 150. A sequence of imaging frames of ultrasound pulses is applied to the body-part 150; the echo signals that are recorded in response to the ultrasound pulses of the different imaging frames—at successive acquisition instants over time during an analysis (time) period (for example, at a frame rate of 4-20 Hz during 2-25 seconds) provide a representation of corresponding locations of the body-part 150 (in a slice thereof at the selected scanning plane) during the analysis period. The echo signals result from the superimposition of different contributions generated by the contrast agent (if present) and the surrounding tissue. Preferably, the ultrasound scanner 100 operates in a contrast-specific imaging mode so as to substantially reduce the dominant (linear) contribution of the tissue in the echo signals, with respect to the (non-linear) contribution of the contrast agent for example, based on harmonic imaging (HI), pulse inversion (PI), power modulation (PM) or other contrast pulse sequencing (CPS) techniques, as described in "Rafter et al., Imaging technologies and techniques, Cardiology Clinics 22 (2004), pp. 181-197" (the entire disclosure of which is herewith incorporated by reference). A corresponding sequence of (contrast-specific) video images is then generated; for each acquisition instant, the video image comprises a digital value for each visualizing element (i.e., pixel) representing a corresponding location of the body-part; the pixel value is defined by an intensity value of the echo signal that has been recorded for the location at that acquisition instant. In this way, the sequence of video images represents an evolution of the perfusion of the body-part 150 during the analysis period.

Figure 2:
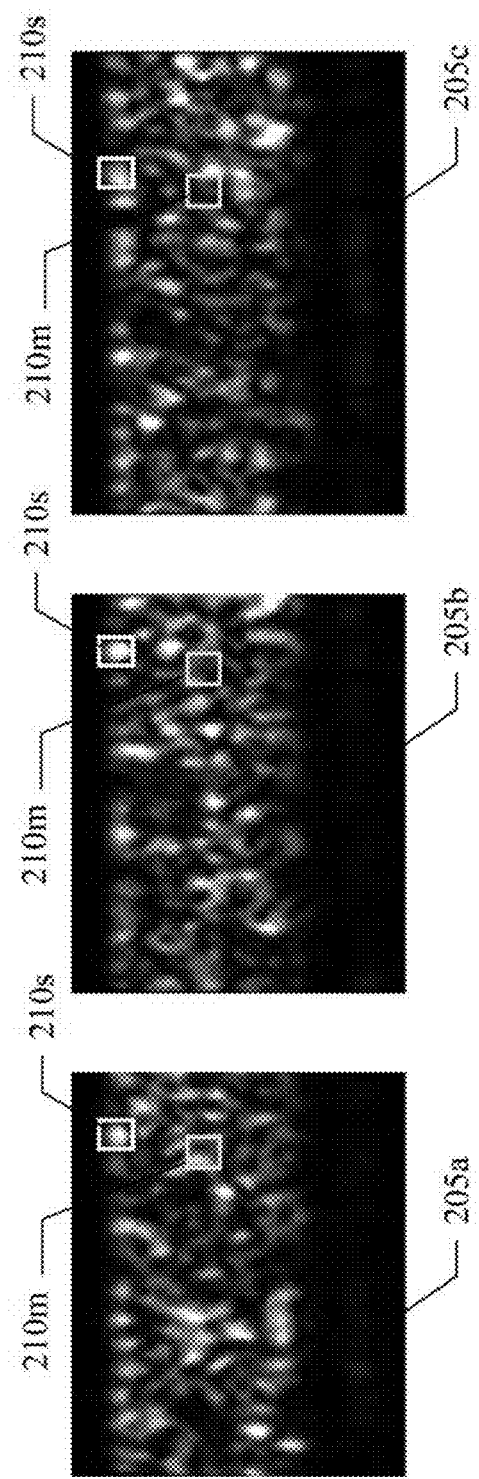
FIG. 2 shows an example of in-vitro scenario for the application of the solution according to an embodiment of the present disclosure.

An example of in-vitro scenario for the application of the solution according to an embodiment of the present disclosure is shown in the FIG. 2.

Particularly, (phospholipid-stabilized) microbubbles were made to circulate at a mean flow velocity of 1 mm/s through a tube with a diameter of 3 mm contained within a tissue mimicking flow phantom. The corresponding sequence of video images was acquired with a Sequoia ultrasound scanner by Siemens Medical Systems (trademarks) in the CPS mode at a frame rate of 4 Hz over 25 seconds (i.e., 100 imaging frames). The video images corresponding to the imaging frames No. 25, No. 43 and No. 66 are indicated in the figure with the references 205a, 205b and 205c, respectively. As may be seen, the microbubbles at an upper wall of the tube are substantially static because of laminar flow conditions—for example, as visible for the region denoted with the reference 210s; conversely, the microbubbles at a center of the tube (spaced apart from its upper wall) move with the mean flow velocity—for example, as visible for the region denoted with the reference 210m.

In the solution according to an embodiment of the present disclosure, as described in detail in the following, the segmentation (in this case, among the pixels of the static microbubbles and the pixels of the moving microbubbles) is based on a statistical analysis of the pixel values over time.

Figure 3A:
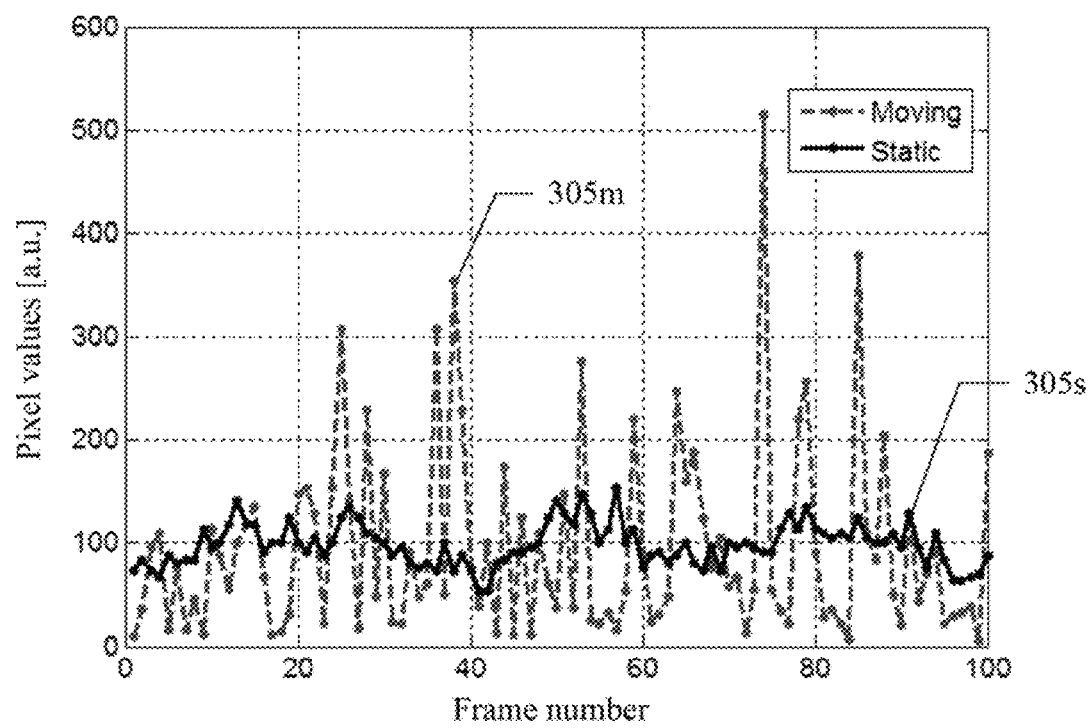
FIG. 3A-FIG. 3B show an example of application of the solution according to an embodiment of the present disclosure.
Figure 3B:
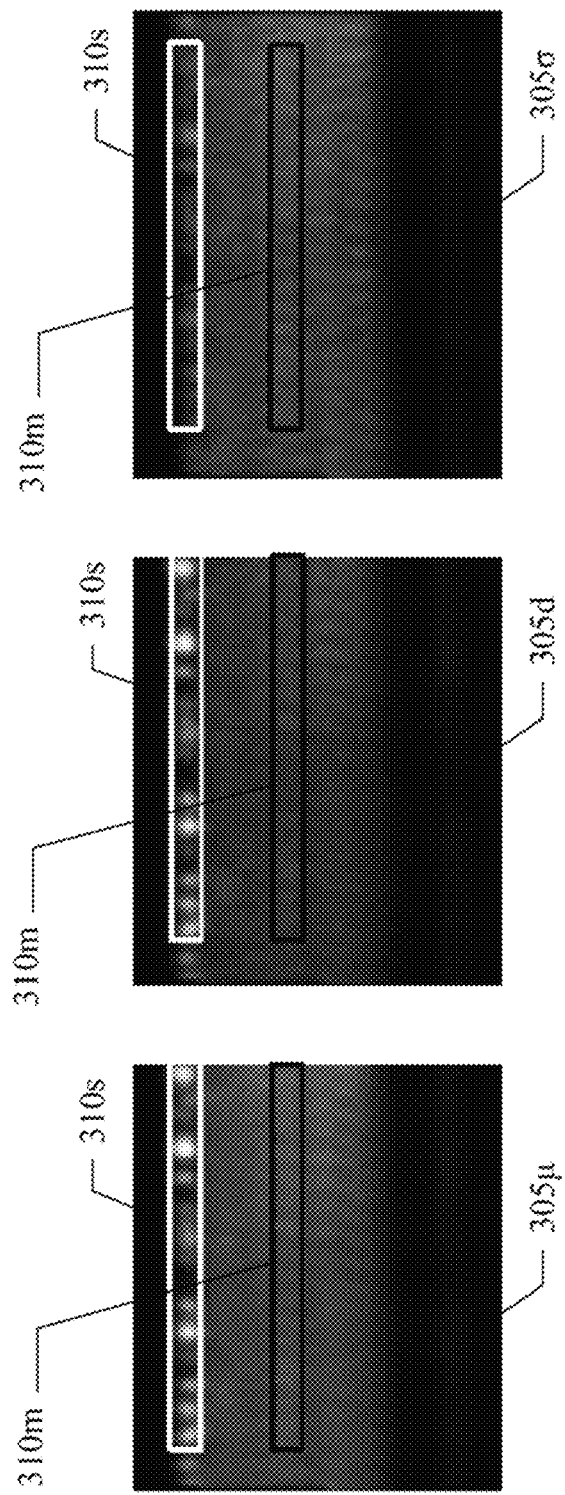

Particularly, an example of application of the solution according to an embodiment of the present disclosure is shown in the FIG. 3A-FIG. 3B.

Starting from the FIG. 3A, the (linearized) pixel values for a representative pixel in the region of the static microbubbles and in the region of the moving microbubbles are represented by a curve 305s (solid line) and by a curve 305m (dotted line), respectively, in a common diagram plotting the pixel values on the ordinate axis (arbitrary units, a.u.) against the frame numbers on the abscissa axis (adimensional).

As may be seen, the dynamics of the pixel values over time for the pixel of the static microbubbles (curve 305s) and for the pixel of the moving microbubbles (curve 305m) are substantially different; particularly, the curve 305s for the static microbubbles is almost constant, whereas the curve 305m for the moving microbubbles exhibits high variations (due to the appearance and disappearance of the microbubbles). Therefore, a statistical parameter of a statistical distribution of the pixel values over time of each pixel may be used to discriminate them.

For example, for each pixel the (arithmetic) mean, the median and the standard deviation of its statistical distribution are calculated.

Particularly, the mean $\overline{X}$ of a statistical variable having discrete values $X_i$, with $i=1 \ldots N$ (i.e., the pixel values over time in this case) is equal to:

$$\overline{X} = \frac{1}{N} \sum_{i=1}^{N} X_i;$$

the mean $\overline{X}$ is a central-tendency statistical parameter (i.e., indicating a value around which the statistical variable values cluster) that represents an expected value of the statistical variable when it has a statistical distribution with a symmetric shape.

The median $\tilde{X}$ of the same statistical variable $X_i$ (sorted from the smallest one $X_1$ to the largest one $X_N$ of its values) is equal to:

$$\tilde{X} = X_{(N+1)/2} \text{ if } N \text{ is odd}$$

$$\tilde{X} = (X_{N/2} + X_{N/2+1})/2 \text{ if } N \text{ is even};$$

the median $\tilde{X}$ is another central-tendency statistical parameter that represents the expected value of the statistical variable when it has a statistical distribution with a skewed (i.e., asymmetric) shape.

The standard deviation σ of the same statistical variable $X_i$ is equal to:

$$\sigma = \sqrt{\frac{1}{N} \sum_{i=1}^{N} (X_i - \overline{X})^2} \; ;$$

the standard deviation σ is a dispersion statistical parameter (i.e., indicating a variability or spread of the statistical variable values) that represents how the statistical variable values disperse from their expected value.

With reference now to the FIG. 3B, these statistical parameters may be used to segment the video images of the FIG. 2, so as to discriminate the static microbubbles and the moving microbubbles. For this purpose, three different parametric images 305μ, 305d and 305σ are calculated. Particularly, the parametric images 305μ, 305d and 305σ have the same size as the video images; each pixel of the parametric images 305μ, 305d and 305σ has a parameter value equal to the value of the mean, the median and the standard deviation, respectively, of the corresponding pixel values over time.

As may be seen, the contrast (or difference) between the pixels of the static microbubbles and the pixels of the moving microbubbles (for example, as visible for the regions denoted with the references 310s and 310m, respectively) considerably improves. Particularly, in the parametric images 305μ, for the mean and in the parametric image 305d for the median the parameter values are higher in the pixels of the static microbubbles (region 310s) and lower in the pixels of the moving microbubbles (region 310m); this is due to the fact that the expected value of the pixel values (as expressed by the mean and the median) is higher in the pixels of the static microbubbles than in the pixels of the moving microbubbles. The contrast is higher in the parametric image 305d for the median than in the parametric image 305μ for the mean, since in the pixels of the moving microbubbles the outliers of their pixel values (pulling the mean towards the values thereof) do not influence the median. Conversely, in the parametric image 305σ for the standard deviation the parameter values are lower in the pixels of the static microbubbles (region 310s) and higher in the pixels of the moving microbubbles (region 310m); this is due to the fact that the pixel values are less dispersed over time in the pixels of the static microbubbles than in the pixels of the moving microbubbles. For example, the contrast between the static microbubbles and the moving microbubbles may be measured by calculating a ratio between an average of the parameter values of the corresponding pixels. Particularly, this ratio is equal to 1.69 in the parametric image 305μ for the mean, to 2.72 in the parametric image 305d for the median and to 0.84 in the parametric image 305σ for the standard deviation; this confirms that the statistical parameter providing the best results is the median (followed by the mean and the standard deviation).

The above-mentioned parameter values (and especially the median values) may be used to segment the original images with a thresholding technique. For example, a segmentation threshold for the parametric values may be set equal to the mean between the average of the parameter values of the pixels of the static microbubbles and the average of the parameter values of the pixels of the moving microbubbles (manually selected); each pixel is then assigned to a segment of the static microbubbles when its parameter value is higher than the segmentation threshold or to a segment of the moving microbubbles otherwise.

Generally, the above-described solution facilitates the segmentation, with a beneficial effect on the accuracy of the obtained results.

Particularly, this solution may be used to improve the performance of the quantitative characterization of lesions in DCE-US imaging applications. For example, this allows excluding (or at least substantially reducing) the contribution of hypo-perfused portions (for example, with necrotic tissues) in the analysis region comprising the lesion to be analyzed and/or the contribution of hyper-perfused portions (for example, with big blood vessels) in the control region comprising healthy tissue to be compared with the lesion. As a result, the corresponding errors that might reflect in the relative consolidated value of the analysis region are significantly reduced (so that the segmentation is more reproducible even when the analysis/control regions are selected manually by the operator, since its quality is now less dependent on personal skills and experiences).

Moreover, the same solution may also be used to improve the detection and quantification of immobilized particles of a target-specific contrast agent in UMI applications. For example, this allows removing (or at least substantially reducing) the contribution of the circulating particles of the target-specific contrast agent, especially at early times after its administration.

The above-mentioned advantages are particularly perceived in the context of therapeutic follow-up, since they facilitate the identification of even subtle changes in the perfusion of a lesion during its treatment that may be indicative of the effectiveness of the treatment.

As a further improvement, the segmentation may be based on two or more statistical parameters relating to the pixel values over time of each pixel.

Particularly, an example of application of the solution according to a further embodiment of the present disclosure is shown in the FIG. 4A-FIG. 4D.

Figures 4A, 4B:
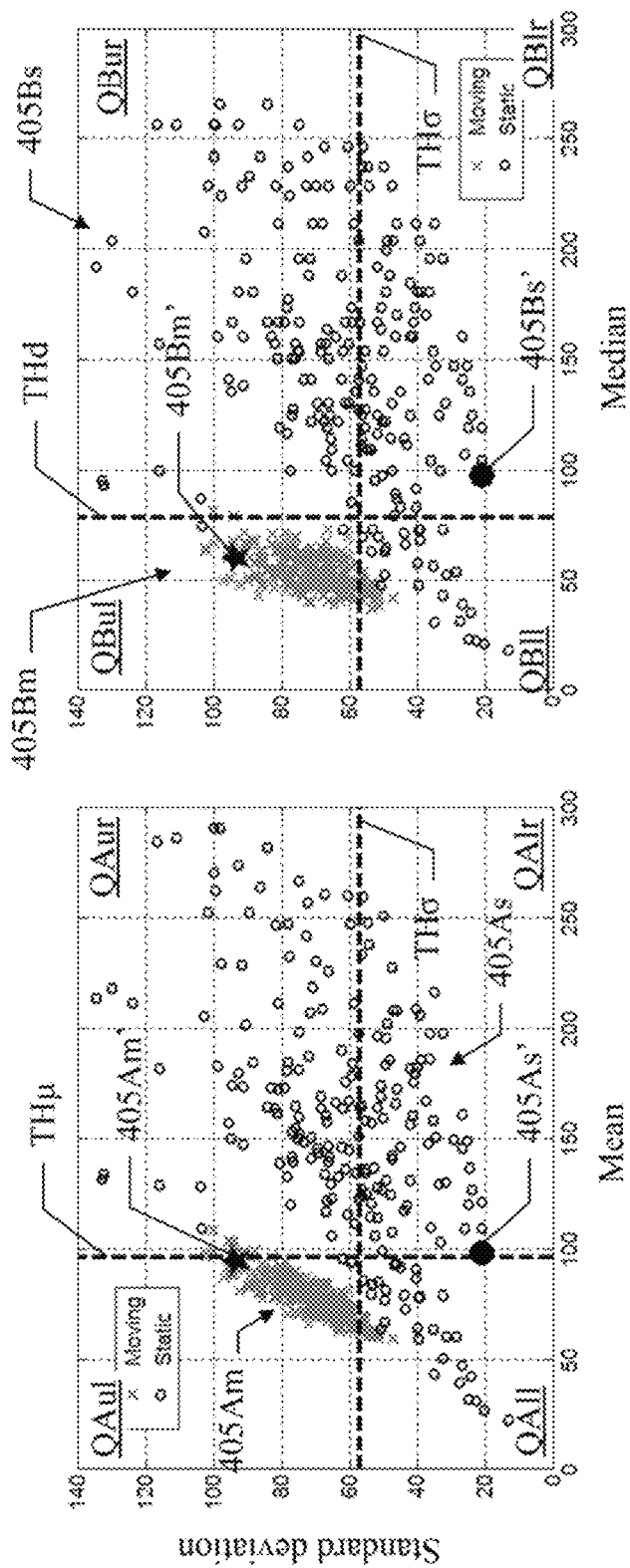
FIG. 4A-FIG. 4D show an example of application of the solution according to a further embodiment of the present disclosure.

Starting from the FIG. 4A, the mean values and the standard deviation values of the pixels in the region of the static microbubbles (310s) and in the region of the moving microbubbles (310m) of the FIG. 3B are represented by points 405As (circles) and by points 405Am (crosses), respectively, in a common scatter diagram plotting the mean values on the abscissa axis and the standard deviation values on the ordinate axis (adimensional); particularly, the points denoted with the references 405As' (black filled circle) and 405Am' (black filled star) correspond to the representative pixel in the region of the static microbubbles (210s) and to the representative pixel in the region of the moving microbubbles (210m) of the FIG. 2, respectively.

A segmentation threshold $TH\mu=97$ for the mean values and a segmentation threshold $TH\sigma=57$ for the standard deviation values are calculated (for example, by averaging the corresponding parameter values of the points 405As' and 405Am'). The segmentation thresholds $TH\mu$ and $TH\sigma$ define four segmentation quadrants in the scatter diagram. Particularly, an upper-right segmentation quadrant QAur is defined by a segmentation criterion (mean value>$TH\mu$ AND standard deviation value>$TH\sigma$), an upper-left segmentation quadrant QAul is defined by a segmentation criterion (mean value≤$TH\mu$ AND standard deviation value>$TH\sigma$), a lower-left segmentation quadrant QAll is defined by a segmentation criterion (mean value≤$TH\mu$ AND standard deviation value≤$TH\sigma$) and a lower-right segmentation quadrant QAlr is defined by a segmentation criterion (mean value>$TH\mu$ AND standard deviation value≤$TH\sigma$).

Likewise, in the FIG. 4B the median values and the standard deviation values of the pixels in the region of the static microbubbles (310s) and in the region of the moving microbubbles (310m) of the FIG. 3B are represented by points 405Bs (circles) and by points 405Bm (crosses), respectively, in another common scatter diagram plotting the median values on the abscissa axis and the standard deviation values on the ordinate axis (adimensional); particularly, the points denoted with the references 405Bs' (black filled circle) and 405Am' (black filled star) correspond to the representative pixel in the region of the static microbubbles (210s) and to the representative pixel in the region of the moving microbubbles (210m) of the FIG. 2, respectively.

A segmentation threshold THd=79 for the median values is calculated as above in addition to the same segmentation threshold $TH\sigma=57$ for the standard deviation values. The segmentation thresholds THd and $TH\sigma$ define other four segmentation quadrants in the scatter diagram. Particularly, an upper-right segmentation quadrant QBur is defined by a segmentation criterion (median value>THd AND standard deviation value>$TH\sigma$), an upper-left segmentation quadrant QBul is defined by a segmentation criterion (median value≤THd AND standard deviation value>$TH\sigma$), a lower-left segmentation quadrant QBll is defined by a segmentation criterion (median value≤THd AND standard deviation value≤$TH\sigma$) and a lower-right segmentation quadrant QBlr is defined by a segmentation criterion (median value>THd AND standard deviation value≤$TH\sigma$).

As may be seen by comparing the scatter diagrams of the FIG. 4A-FIG. 4B, the contrast between the pixels of the static microbubbles and the pixels of the moving microbubbles is higher in the scatter diagram of the FIG. 4B for the median/standard deviation than in the scatter diagram of the FIG. 4A for the mean/standard deviation (for example, as clearly evident for the points 405Bm',405Bs' in the FIG. 4B with respect to the points 405Am',405As' in the FIG. 4A); this confirms that the statistical parameter providing the better results in combination with the standard deviation is again the median.

The above-mentioned parameter values may be used to segment the original images according to the corresponding segmentation criteria.

Figure 4C:
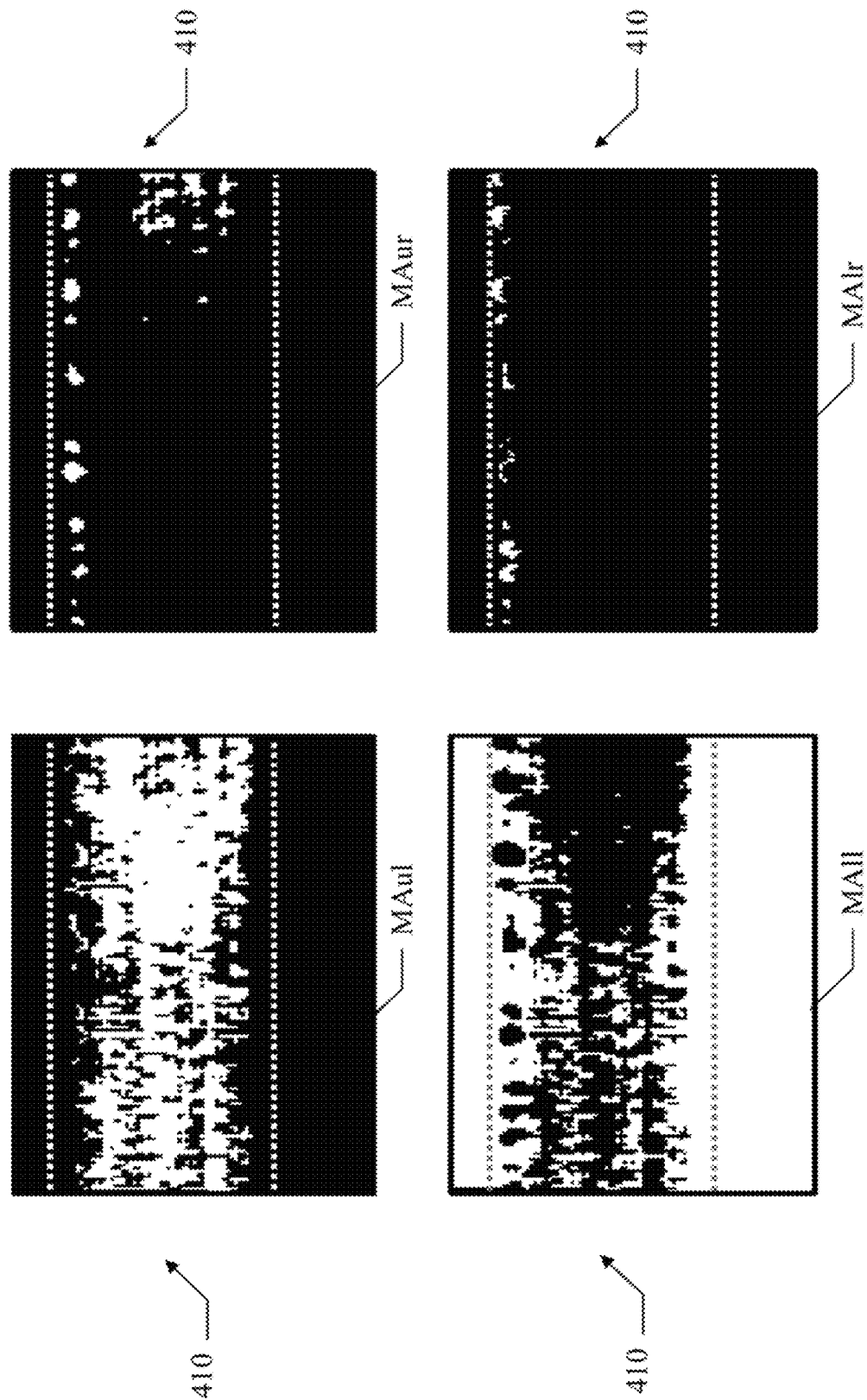

For example, as shown in the FIG. 4C, four segmentation masks MAur, MAul, MAll and MAlr are built using the segmentation criteria corresponding to the segmentation quadrants QAur, QAul, QAll and QAlr, respectively, of the FIG. 4A for the mean/standard deviation. Each segmentation mask MAur, MAul, MAll and MAlr has the same size as the video images; the pixels with parameter values that fulfill the corresponding segmentation criterion are white, whereas the other pixels are black. Moreover, in all the segmentation masks MAur, MAul, MAll and MAlr a region 410 represents the 3-mm tube of the flow phantom used to acquire the video images (delimited by two dashed lines representing its wall).

As may be seen, the white pixels in the segmentation masks MAur and MAlr detect part of the pixels of the static microbubbles at the upper wall of the tube 410 (even if some white pixels at the center of the tube 410 are present in the segmentation mask MAur); on the other hand, the white pixels in the segmentation masks MAul and MAll detect part of the pixels of the moving microbubbles at the center of the tube 410 (with the white pixels outside the tube 410 in the segmentation mask MAll that are probably due to noise and phantom tissue signals).

Figure 4D:
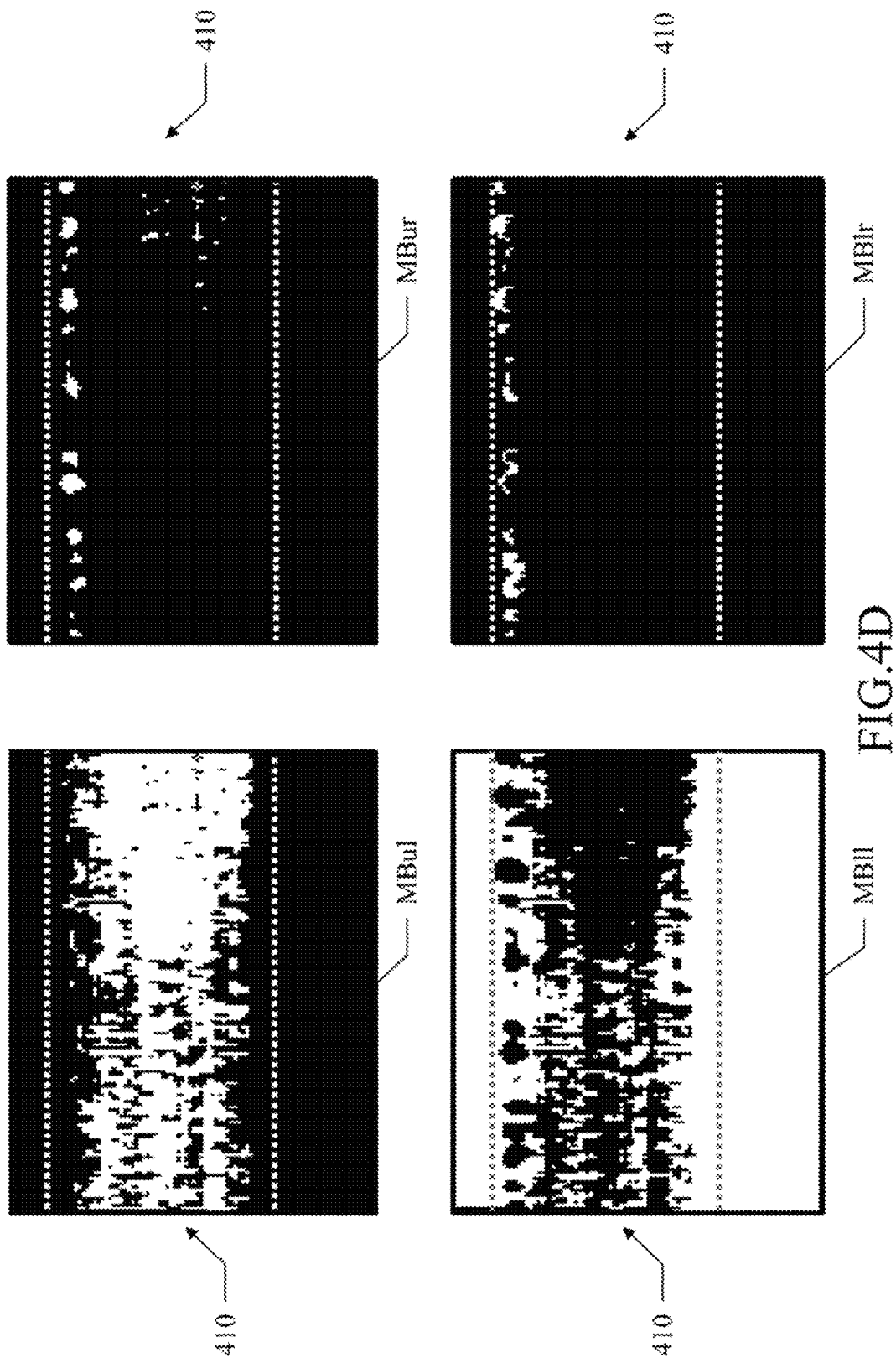

Likewise, in the FIG. 4D other four segmentation masks MBur, MBul, MBll and MBlr are built as above using the segmentation criteria corresponding to the segmentation quadrants QBur, QBul, QBll and QBlr, respectively, of the FIG. 4B for the median/standard deviation (with the same region of the tube that is again identified by the reference 410). As above, the white pixels in the segmentation masks MBur and MBlr detect part of the pixels of the static microbubbles at the upper wall of the tube 410 (even if some white pixels at the center of the tube 410 are present, but to a lower extent, in the segmentation mask MBur); on the other hand, the white pixels in the segmentation masks MBul and MBll detect part of the pixels of the moving microbubbles at the center of the tube 410 (with the white pixels outside the tube 410 in the segmentation mask MBll that are again probably due to noise and phantom tissue signals).

As may be seen by comparing the segmentation masks of the FIG. 4C-FIG. 4D, the segmentation between the pixels of the static microbubbles and the pixels of the moving microbubbles is better in the segmentation masks of the FIG. 4D for the median/standard deviation than in the segmentation mask of the FIG. 4C for the mean/standard deviation—for example, as clearly evident for the segmentation mask MBur in the FIG. 4D with respect to the segmentation mask MAur in the FIG. 4C; this again confirms that the statistical parameter providing the better results in combination with the standard deviation is the median.

As a still further improvement, the segmentation may be based on the above-mentioned statistical parameters relating to the pixel values over time of each pixel, which are transformed to provide a (transformed) statistical distribution of the (transformed) pixel values with a skewed shape.

Figure 5A:
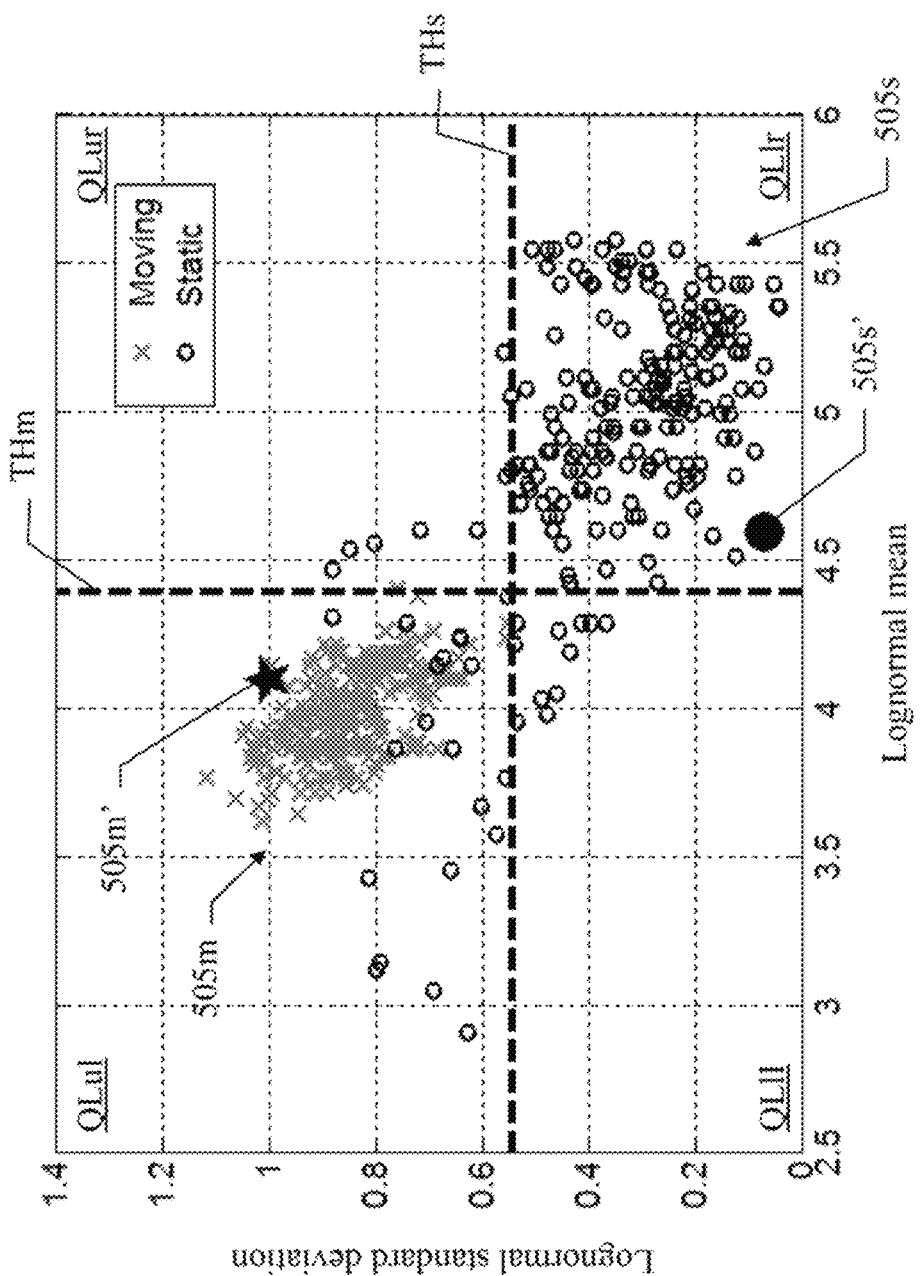
Figure 5C:
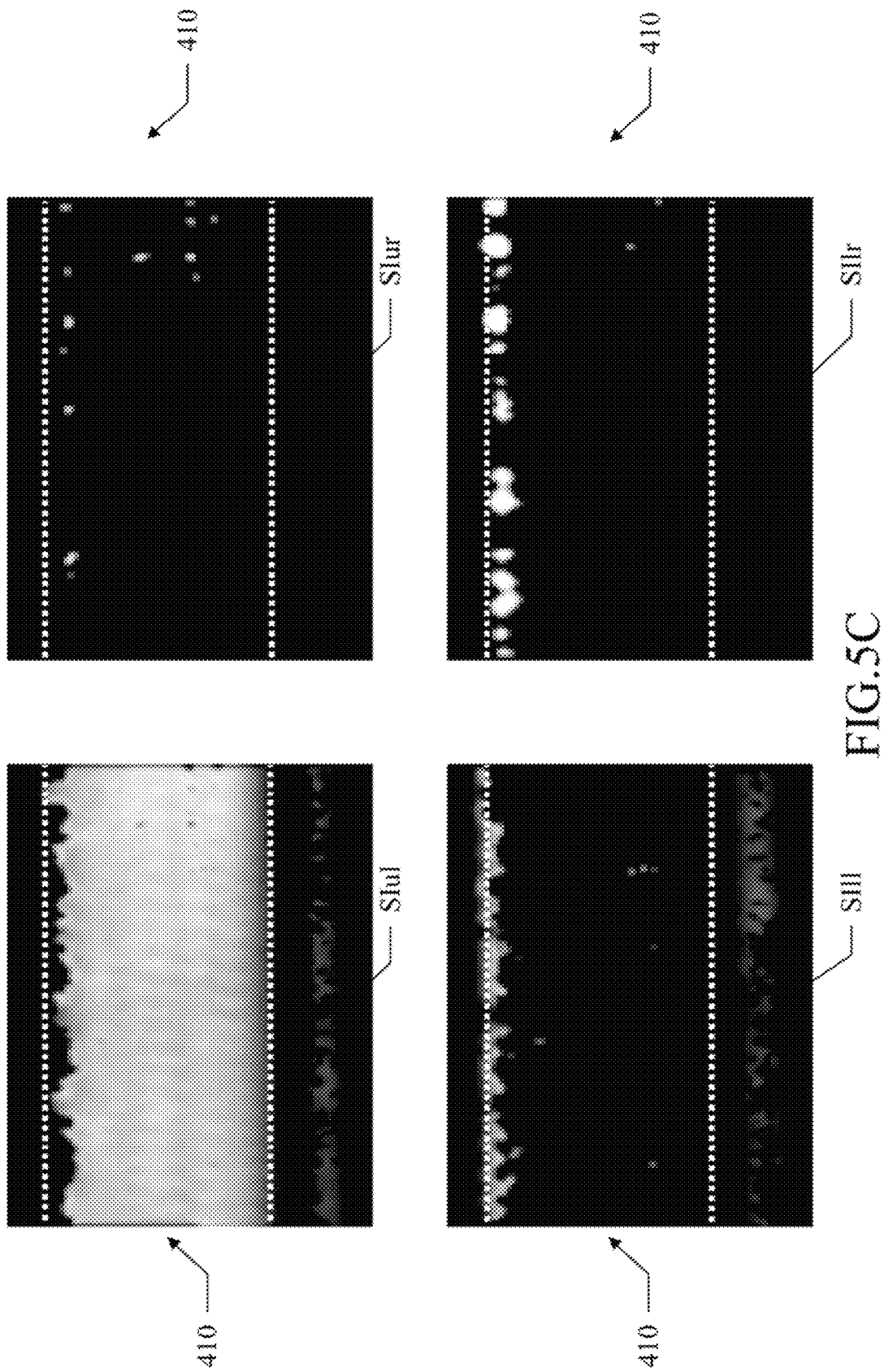

Particularly, an example of application of the solution according to a further embodiment of the present disclosure is shown in the FIG. 5A-FIG. 5C.

Starting from the FIG. 5A, the (transformed) statistical distribution is assumed to be a lognormal statistical distribution. In a lognormal statistical distribution, the natural logarithm of the statistical variable has a normal statistical distribution. Particularly, in the case of a continuous statistical variable X, a statistical density function representing the (continuous) normal statistical distribution is a normal statistical density function (or simply normal function):

$$P_{normal} = \frac{1}{\sigma\sqrt{2\pi}} \exp\left(\frac{-(X-\overline{X})^2}{2\sigma^2}\right),$$

wherein the same symbols $\overline{X}$ and $\sigma$ are used to indicate the mean and the standard deviation, respectively, of the statistical variable X; therefore, the statistical density function representing the (continuous) lognormal statistical distribution is a lognormal statistical density function (or simply lognormal function):

$$P_{lognormal} = \frac{1}{s\sqrt{2\pi}\,X}\exp\left[\frac{-(\ln(X)-m)^2}{2s^2}\right],$$

wherein m and s now are the mean and the standard deviation, respectively, of the natural logarithm of the statistical variable X (i.e., ln(X)).

In this case, the (lognormal) mean m and the (lognormal) standard deviation s may be calculated directly from the (normal) mean $\overline{X}$ and the (normal) median $\tilde{X}$ by applying the following transformation formulas:

$$m = \ln(\tilde{X}),$$

$$s = \sqrt{2\ln\left(\frac{\overline{X}}{\tilde{X}}\right)}$$

if $\frac{\overline{X}}{\tilde{X}} > 1$ $s = 0$ if $\frac{\overline{X}}{\tilde{X}} \leq 1.$ The segmentation is now based on the parameter values defined by the lognormal mean and the lognormal standard deviation. For this purpose, the lognormal mean value and the lognormal standard value of each pixel are calculated by applying the above-mentioned transformation formulas to the actual mean value and median value of its pixel values over time. The lognormal mean values and the lognormal standard deviation values of the pixels in the region of the static microbubbles (310s) and in the region of the moving microbubbles (310m) of the FIG. 3B are represented by points 505s (circles) and by points 505m (crosses), respectively, in a common scatter diagram plotting the lognormal mean values on the abscissa axis and the lognormal standard deviation values on the ordinate axis (adimensional); particularly, the points denoted with the references 505s' (black filled circle) and 505m' (black filled star) correspond to the representative pixel in the region of the static microbubbles (210s) and to the representative pixel in the region of the moving microbubbles (210m) of the FIG. 2, respectively.

A segmentation threshold THm=4.4 for the lognormal mean values and a segmentation threshold THs=0.54 for the lognormal standard deviation values are calculated as above. The segmentation thresholds THm and THs define four segmentation quadrants in the scatter diagram. Particularly, an upper-right segmentation quadrant QLur is defined by a segmentation criterion (lognormal mean value>THm AND lognormal standard deviation value>THs), an upper-left segmentation quadrant QLul is defined by a segmentation criterion (lognormal mean value≤THm AND lognormal standard deviation value>THs), a lower-left segmentation quadrant QLll is defined by a segmentation criterion (lognormal mean value≤THm AND lognormal standard deviation value≤THs) and a lower-right segmentation quadrant QLlr is defined by a segmentation criterion (lognormal mean value>THm AND lognormal standard deviation≤valueTHs).

As may be seen, the contrast between the pixels of the static microbubbles and the pixels of the moving microbubbles is further improved; indeed, in this case the points of the static microbubbles and of the moving microbubbles cluster in distinct areas of the scatter diagram with a reduced overlap. This further facilitates the segmentation, since the segmentation thresholds THm,THs may now be defined independently without compromising the performance of the segmentation.

Moving to the FIG. 5B, four segmentation masks MLur, MLul, MLll and MLlr are built as above using the segmentation criteria corresponding to the segmentation quadrants QLur, QLul, QLll and QLlr, respectively, of the FIG. 5A (with the same region of the tube that is again identified by the reference 410).

In this case, the white pixels in the segmentation mask MLlr detect most of the pixels of the static microbubbles at the upper wall of the tube 410; on the other hand, the white pixels in the segmentation masks MLul detect most of the pixels of the moving microbubbles at the center of the tube 410 (with the white pixels outside the tube 410 in the mask MLul that are probably due to an acoustic artifact of the CPS mode in combination with a high concentration of the microbubbles in the tube 410, which acoustic artifact may be reduced by lowering the concentration of the microbubbles). Conversely, most of the pixels of the segmentation masks MLur and MLll are black (with the white pixels outside the tube 410 in the segmentation mask MBll that are again probably due to noise and phantom tissue signals). This confirms that the logarithmic transformation of the pixel values improves the performance of the segmentation.

As shown in the FIG. 5C, the above-defined segmentation masks may be applied to the parametric image 305u of the FIG. 3B (representing the mean values of each pixel). Particularly, four segmented images SIur, SIul, SIll and SIlr are built by applying the segmentation masks MLur, MLul, MLll and MLlr, respectively, of the FIG. 5B on this parametric image; each pixel of the segmented images SIur, SIul, SIll and SIlr is assigned its parameter value, i.e., the mean value (log-compressed with a compression factor of 40 dB for display purposes) if it is white in the corresponding segmentation masks, whereas it remains black otherwise (so as to display the mean values only of the segmented pixels). As a result, the segmented image SIlr primarily shows the pixels of the static microbubbles at the upper wall of the tube 410, whereas the segmented image SIul primarily shows the pixels of the moving microbubbles at the center of the tube 410 (so as to facilitate their discrimination).

Figure 6:
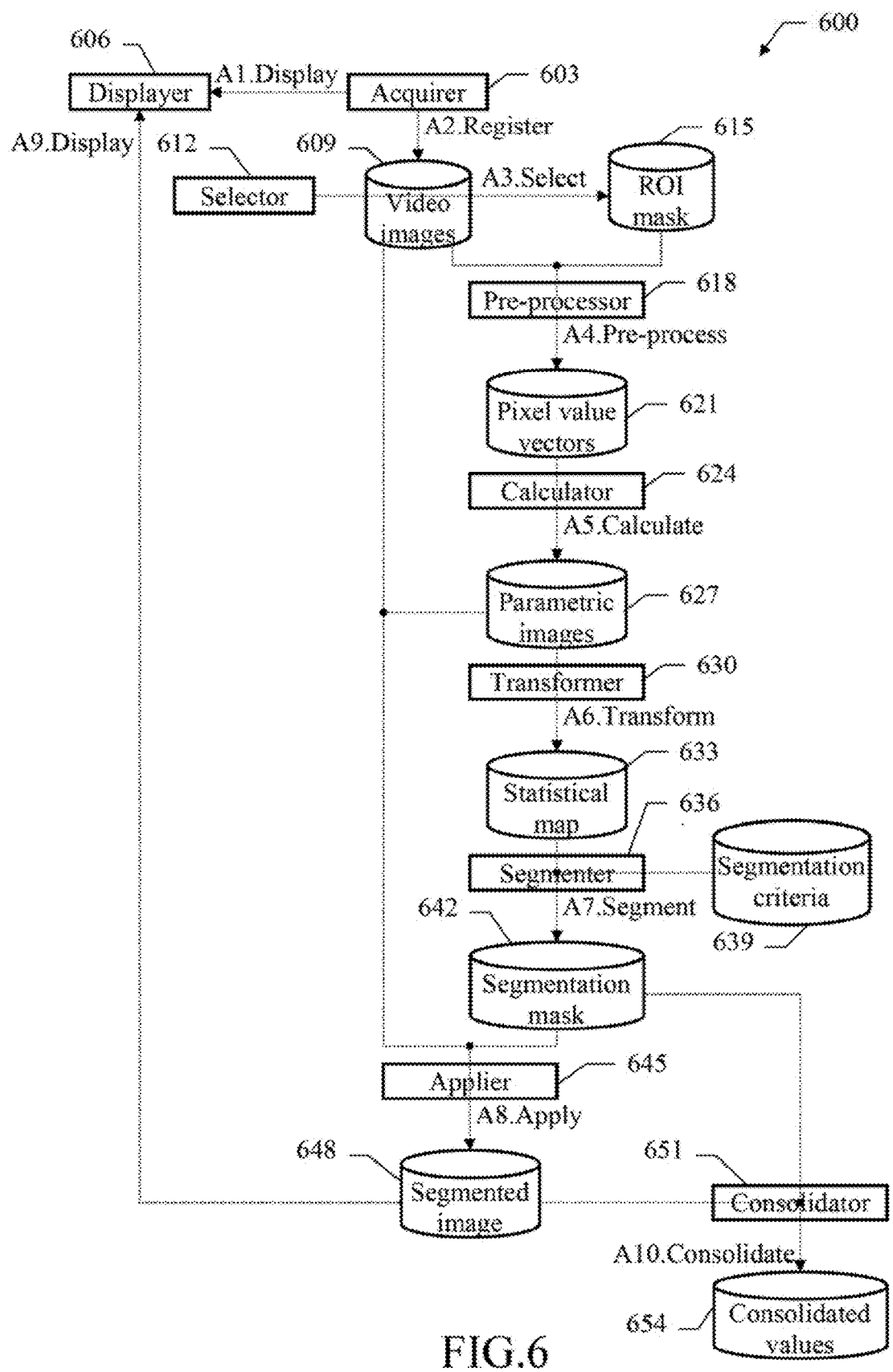
FIG. 6 shows a collaboration diagram representing the roles of the main components that may be used to implement the solution according to an embodiment of the present disclosure.

A collaboration diagram representing the roles of the main components that may be used to implement the solution according to an embodiment of the present disclosure is shown in FIG. 6.

Particularly, all the components are denoted as a whole with the reference 600; the figure describes both the static structure of the components 600 and their dynamic behavior (by means of a series of exchanged messages, each one representing a corresponding action, denoted with sequence numbers preceded by the symbol "A").

The information (programs and data) is typically stored in the hard disk and loaded (at least partially) into the working memory of the ultrasound scanner when the programs are running, together with an operating system and other application programs (not shown in the figure). The programs are initially installed onto the hard disk, for example, from removable disks. In this respect, each one of the components 600 may represent a module, segment or portion of code, which comprises one or more executable instructions for implementing the specified logical function (or more).

More specifically, an acquirer 603 is used to acquire the video images. For this purpose, the acquirer 603 comprises a driver that controls the imaging probe. For example, this imaging probe driver is provided with a transmit beam former and pulsers for generating the imaging frames of ultrasound pulses to be applied to the body-part under analysis at each acquisition instant; the ultrasound pulses have a low acoustic energy (such as with a mechanical index MI=0.01-0.3), so as to induce a negligible destruction of the contrast agent (such as less than 5%, and preferably less than 1% of its local concentration between successive imaging frames). The imaging probe then receives the (analog RF) echo signals that are reflected by the different locations of the body-part (in the selected scanning plane) at each acquisition instant. These analog RF echo signals are supplied to a receive processor, which pre-amplifies the analog RF echo signals and applies a preliminary time-gain compensation (TGC); the analog RF echo signals are then converted into digital values by an Analog-to-Digital Converter (ADC), and combined into focused beam signals through a receive beam former. The digital RF echo signals so obtained are preferably processed through further digital algorithms and other linear or non-linear signal conditioners (for example, a post-beam-forming TGC); particularly, the receive processor applies a contrast-specific algorithm (such as based on the CPS technique) to reduce the contribution of the tissue. The digital RF echo signals are then demodulated, log-compressed (in order to obtain images with well-balanced contrast), scan-converted into a video format and rendered according to a given color-map palette. In this way, a video image for each acquisition instant is generated. The video image is defined by a matrix of cells, each one storing the corresponding pixel value. The pixel value defines the brightness of the pixel; for example, in gray scale video images the pixel value may be coded on 8 bits, increasing from 0 (black) to 255 (white) as a function of the intensity of the corresponding echo signal (representing the acoustic response of the corresponding location of the body-part at that acquisition instant).

At the beginning of the analysis process, an operator of the ultrasound scanner actuates the imaging probe and moves it around the body-part to be analyzed (before administering any contrast agent). The corresponding video images are provided to a displayer 606 as soon as they are acquired; the displayer 606 comprises a driver that controls the monitor of the ultrasound scanner, so as to cause the display of these video images in real-time (action "A1.Display").

The operator chooses a scan plane representing a specific slice of the body-part (for example, comprising a lesion to be analyzed), and keeps the imaging probe fixed in this position for a predefined analysis period. The contrast agent is now administered to the patient and a corresponding sequence of video images (representing the perfusion in the chosen scan plane of the body-part during the analysis period) is acquired as above. These video images (in addition to be displayed in real-time by the displayer 606, whose connection is not shown in the figure for the sake of clarity) are also registered by saving them into a repository 609 (action "A2.Register").

A selector 612 is used by the operator to select, in one arbitrarily-chosen video image of the repository 609, a desired region of interest (ROI) of the body-part to be analyzed. The region of interest is represented with a ROI mask, which comprises a matrix of cells with the same size as the video images; each cell of the ROI mask stores a ROI flag (i.e., a binary value) that is asserted (for example, at the logic value 1) when the corresponding pixel is inside the region of interest (i.e., it has been selected), or it is deasserted (for example, at the logic value 0) otherwise. The ROI mask is saved into a repository 615 (action "A3.Select").

A pre-processor 618 accesses the video images in the repository 609 and the ROI mask in the repository 615. For each video image, the pre-processor 618 processes the pixel value of each cell thereof whose ROI flag in the ROI mask is asserted (i.e., inside the region of interest) so as to make it directly proportional to the corresponding local concentration of the contrast agent. For example, this result may be achieved by applying an inverse palette-luminance table and an inverse log-compression (to reverse the effects of their application by the acquirer 603), and then squaring the values so obtained (as described in WO-A-2004/110279, the entire disclosure of which is herein incorporated by reference). The pre-processor 618 then creates a map of pixel value vectors, which comprises a matrix of cells with the same size as the video images; each cell of the map of pixel value vectors whose ROI flag in the ROI mask is asserted stores a pixel value vector, which comprises a sequence of the corresponding linearized pixel values along the video images (with a length corresponding to the duration of the analysis period). This map of pixel value vectors is saved into a repository 621 (action "A4.Pre-process").

The map of pixel value vectors in the repository 621 is supplied to a calculator 624, which also accesses the ROI mask in the repository 615 (whose connection is not shown in the figure for the sake of clarity). For each cell of the map of pixel value vectors whose ROI flag in the ROI mask is asserted (i.e., inside the region of interest), the calculator 624 calculates the values of the mean and of the median of the sequence of the corresponding (linearized) pixel values. The calculator 624 then creates a parametric image for the mean and a parametric image for the median, each one comprising a matrix of cells with the same size as the video images; each cell of the parametric image for the mean and of the parametric image for the median whose ROI flag in the ROI mask is asserted stores the corresponding mean value and median value, respectively. These parametric images are saved into a repository 627 (action "A5.Calculate").

The parametric images in the repository 627 are supplied to a transformer 630, which also accesses the ROI mask in the repository 615 (whose connection is not shown in the figure for the sake of clarity). For each pixel of the parametric images whose ROI flag in the ROI mask is asserted (i.e., inside the region of interest), the transformer 630 calculates the values of the lognormal mean and of the lognormal standard deviation from the corresponding mean value and median value by applying the corresponding transformation formulas. The transformer 630 then creates a statistical map, comprising a matrix of cells with the same size as the video images; each cell of the statistical map whose ROI flag in the ROI mask is asserted stores the corresponding statistical parameters (i.e., the lognormal mean value and lognormal standard deviation value). This statistical map is saved into a repository 633 (action "A6.Transform").

The statistical map in the repository 633 is supplied to a segmenter 636, which also accesses the ROI mask in the repository 615 (whose connection is not shown in the figure for the sake of clarity). The segmenter 636 extracts a selected segmentation criterion (or more) from a repository 639, which stores a number of pre-determined segmentation criteria based on segmentation thresholds for the lognormal mean values and the lognormal standard deviation values;

for example, these segmentation thresholds may have been set during a learning phase by analyzing sample body-parts with well-known characteristics. For each pixel of the statistical map whose ROI flag in the ROI mask is asserted (i.e., inside the region of interest), the segmenter 636 verifies whether the corresponding statistical parameters fulfill the selected segmentation criterion (meaning that it belongs to a corresponding segment representing a portion of the body-part with corresponding homogenous characteristics). The segmenter 636 then creates a segmentation mask for the selected segmentation criterion, comprising a matrix of cells with the same size as the video images; each cell of the segmentation mask stores a segmentation flag (i.e., a binary value) that is asserted when the corresponding segmentation criterion is fulfilled (i.e., the corresponding pixel belongs to the segment) or it is deasserted otherwise. Each segmentation mask so created is saved into a repository 642 (action "A7.Segment").

An applier 645 extracts a selected segmentation mask (or more) from the repository 642; the applier 645 also extracts a selected parametric image (or more) from the repository 627 and/or a selected video image (or more) from the repository 609. The applier 645 applies the (selected) segmentation mask to the (selected) parametric/video image by multiplying them cell-by-cell. This operation creates a segmented image, comprising a matrix of cells with the same size as the video/parametric images; each cell of the segmented image belonging to the segment defined by the segmentation mask (i.e., whose segmentation flag is asserted) stores the corresponding parametric/pixel value, while the other cells are reset to 0. Each segmented image so created is saved into a repository 648 (action "A8.Apply").

Each segmented image in the repository 648 may now be passed to the displayer 606 for its display and any next use thereof (action "A9.Display"). For example, a segmented image discriminating immobilized particles from remaining circulating particles of a target-specific contrast agent may be used to detect the immobilized particles and hence to identify a corresponding lesion in the body-part. In addition or in alternative, a consolidator 651 may extract a selected segmentation mask (or more) from the repository 642 and/or a selected segmented image (or more) from the repository 648. The consolidator 651 calculates a consolidated value (or more) of the portion of the body-part represented by the segment defined by the (selected) segmentation mask/segmented image; for example, the consolidated value may be set equal to the number of the segmentation flags that are asserted in the segmentation mask (measuring the portion of the body-part), or the consolidated value may be set equal to the sum or the average of the pixel/parameter values of the segmented image (characterizing the portion of the body-part). Each consolidated value so calculated is saved into a repository 654 for next use (action "A10.Consolidate"). For example, the average of the parameter values of a ROI relating to an analysis region comprising a lesion to be analyzed in a segmented image wherein the hypo-perfused portions are negatively discriminated is automatically not affected by their contribution, and the average of the parameter values of a ROI relating to a control region comprising healthy tissue to be compared with a lesion in a segmented image wherein the hyper-perfused portions are negatively discriminated is automatically not affected by their contribution; therefore, these consolidated values may be combined into a consolidated value of the analysis region expressed in relative terms with respect to the consolidated value of the control region (for example, equal to their ratio).

Moreover, the number of segmentation flags that are asserted in a segmentation mask discriminating immobilized particles of a target-specific contrast agent and the sum of the pixel/parameter values in a segmented image again discriminating immobilized particles of a target-specific contrast agent, both of them quantify these immobilized particles.

Figure 7:
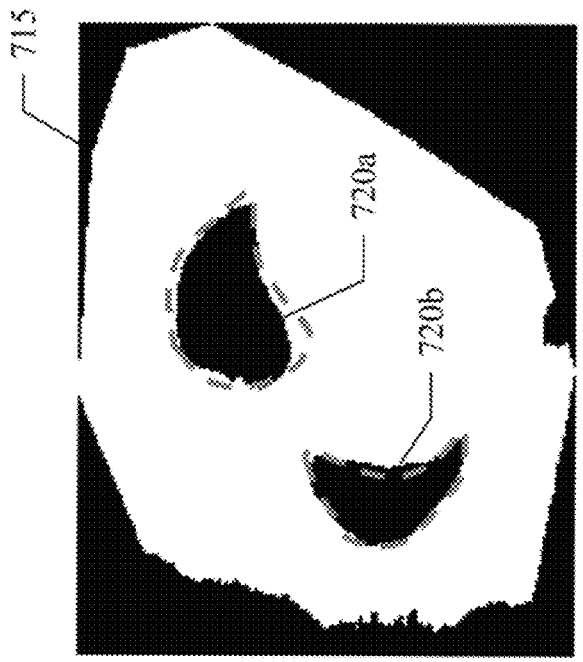
FIG. 7, FIG. 8 and FIG. 9 show different examples of in-vivo applications of the solution according to an embodiment of the present disclosure.
Figure 7:
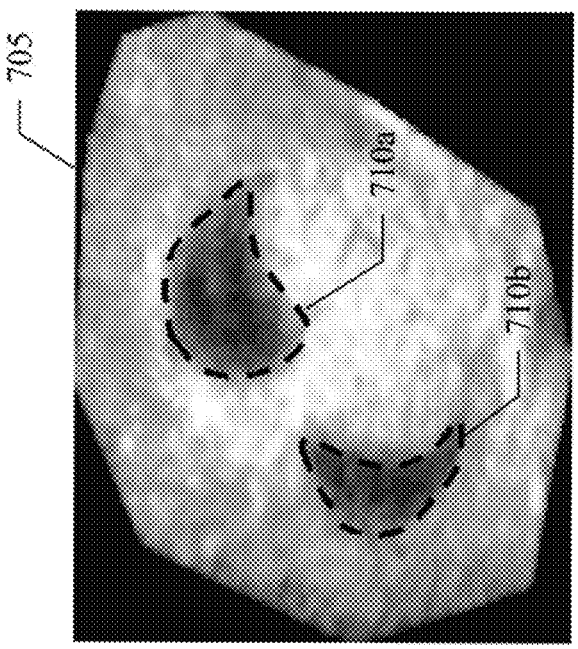
Figure 8:
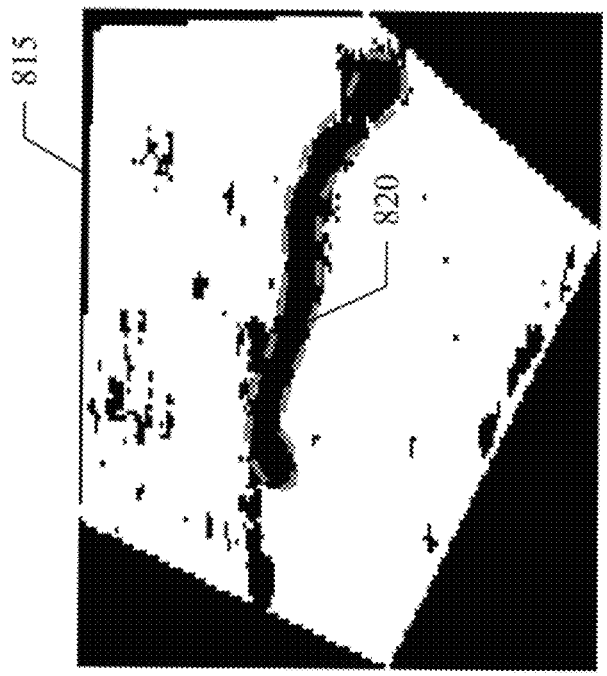
Figure 8:
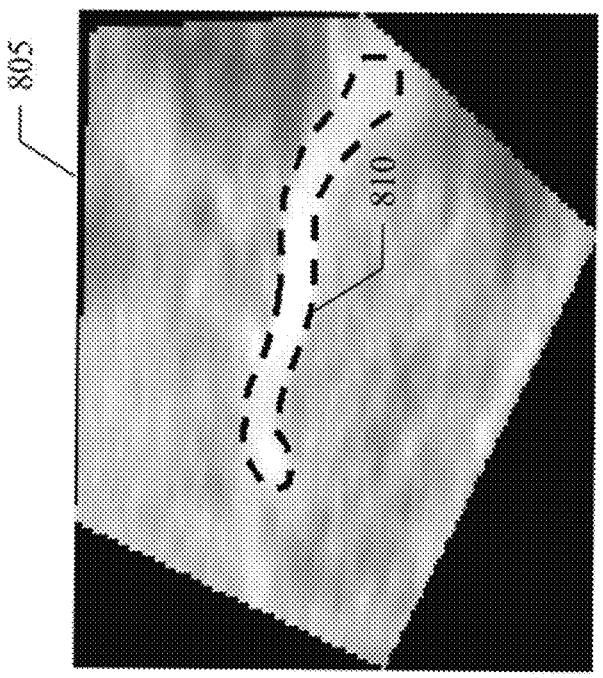
Figure 9:
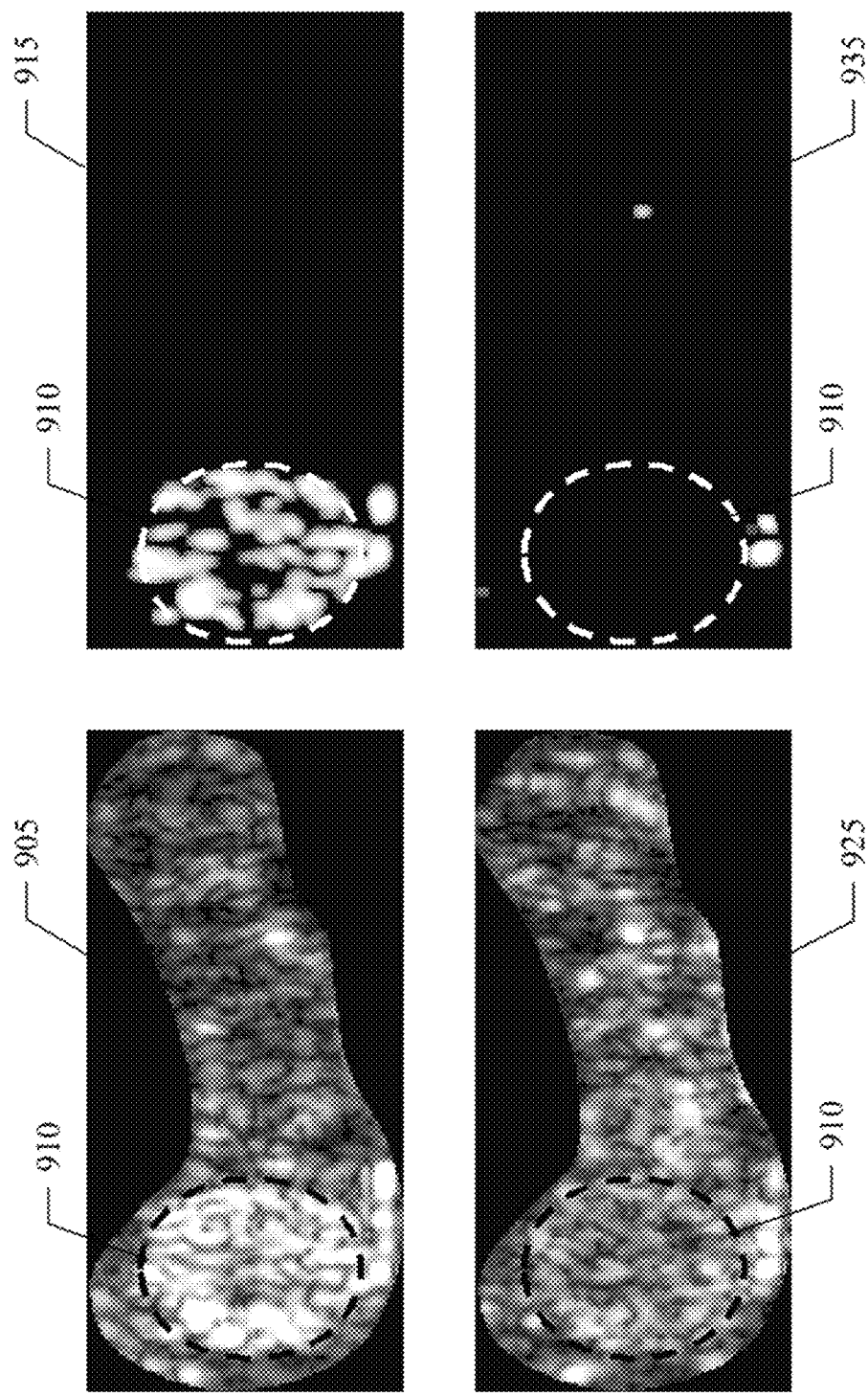

Different examples of in-vivo applications of the solution according to an embodiment of the present disclosure are shown in the FIG. 7, FIG. 8, and FIG. 9.

Starting from the FIG. 7, a video image 705 of a liver tumor was acquired in the contrast-specific imaging mode 20 seconds after the injection of the contrast agent (during peak opacification); two (hypo-perfused) regions 710a and 710b (being darker) were manually outlined on the video image 705.

A segmentation mask 715 was created from a sequence of 100 video images of the liver tumor acquired over 12.5 seconds around the acquisition instant of the video image 705, with the segmentation criterion (lognormal mean value>5.0 AND lognormal standard deviation value>0). As may be seen, the segmentation mask 715 excludes two regions 720a and 720b (black) that substantially correspond to the hypo-perfused regions 710a and 710b, respectively, as confirmed by the good overlap between the excluded regions 720a,720b and the contours of the hypo-perfused regions 710a,710b reported in dashed gray lines on the segmentation mask 715.

Moving to the FIG. 8, a video image 805 of healthy tissue of a liver to be used as a reference region was acquired as above; a (hyper-perfused) region 810 (being lighter) corresponding to a big blood vessel was manually outlined on the video image 805.

A segmentation mask 815 was created from a sequence of 25 video images of the liver acquired over 3 seconds around the acquisition instant of the video image 805, with the segmentation criterion (lognormal mean value<5.9 AND lognormal standard deviation value>0). As may be seen, the segmentation mask 815 excludes a region 820 (black) that substantially corresponds to the hyper-perfused region 810, as confirmed by the good overlap between the excluded region 820 and the contour of the hyper-perfused region 810 reported in dashed gray lines on the segmentation mask 815.

With reference at the end to the FIG. 9, a video image 905 of a prostate of a model rat with an (adenocarcinoma) tumor was acquired in the contrast-specific imaging mode 2 minutes after the injection of a target-specific contrast agent for the vascular cell adhesion molecule 1 (VCAM-1); a tumor region 910 (being lighter) was manually outlined on the video image 905.

A segmentation mask was created from a sequence of 60 video images of the prostate acquired over 15 seconds after the acquisition instant of the video image 905, with the segmentation criterion (lognormal mean value>4.4 AND lognormal standard deviation value>0.54); a segmented image 915 was then created by applying this segmentation mask to a parametric image for the mean created from the same sequence of video images as above. As may be seen, the segmented image 915 substantially shows the immobilized particles of the target-specific contrast only in the tumor region 910, with the remaining circulating particles of the target-specific contrast agent present outside the tumor region 910 in the video image 905 that are substantially absent in the segmented image 915. Moreover, also in the tumor region 910 the remaining circulating particles of the target-specific contrast are substantially removed (as evident by comparing it with the tumor region 910 in the video image 905).

As a control, another video image 925 was acquired in the same conditions but now using a (non-targeted) contrast agent, and a corresponding segmented image 935 was created as above.

In this case, substantially no (circulating/immobilized) particles of the contrast agent are visible (both inside and outside the tumor region 910) in the segmented image 935.

Modifications

Naturally, in order to satisfy local and specific requirements, a person skilled in the art may apply to the solution described above many logical and/or physical modifications and alterations. More specifically, although this solution has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the disclosed solution may be incorporated in any other embodiment as a matter of general design choice. In any case, ordinal or other qualifiers are merely used as labels to distinguish elements with the same name but do not by themselves connote any priority, precedence or order. Moreover, the terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), and the term a/an should be intended as one or more items (unless expressly indicated otherwise).

For example, an embodiment provides a data-processing segmentation method for use in diagnostic imaging applications. The method comprises the following steps. A representation over a non-zero analysis time period of a body-part (being perfused with a contrast agent) is provided; the representation comprises, for each location of a set of locations of the body-part, an indication of a response over the analysis time period of the location to an interrogation signal. For each selected location of a set of selected locations, the value is calculated of at least one statistical parameter of a statistical distribution of the response over the analysis time period of the selected location; the set of selected locations comprises all the locations or a part thereof. The selected locations are segmented according to a comparison between the values of said at least one statistical parameter for the selected locations with at least one segmentation threshold.

However, the representation of the body-part may be provided in any way (see below), so as to provide a representation thereof over an analysis time period having any non-zero length (long enough to be statistically significant); the representation may relate to any type of perfusion (for example, based on a continuous infusion with a destruction flash) of any type of contrast agent (either of the non-targeted or of the targeted type). The method may be applied at the level of any type of locations (for example, pixels, voxels or groups thereof); particularly, it is also possible to sub-sample the representations spatially, determine the segmentation on the sub-sampled representations, and then restore the full-size of the segmentation with interpolation techniques for its application on the original representations. Moreover, the method may be applied to any selected locations (for example, in one or more regions of interest defined in any way), or even to the whole representation of the body-part. The statistical parameters may be of any type and in any number (see below); moreover, the selected locations may be segmented in any number of segments (two or more) according to any comparison between the values of the statistical parameter(s) with any type and number of segmentation thresholds (see below).

In an embodiment, said step of providing a representation over a non-zero analysis time period of a body-part includes providing a sequence of digital images of the body-part registered during the analysis time period; each digital image comprises an intensity value for each location based on the response of the location at a corresponding acquisition instant in the analysis time period. Said step of calculating the value of at least one statistical parameter includes calculating the value of said at least one statistical parameter from the intensity values of the selected location along the digital images.

However, the digital images may be registered in any way (for example, by pre-processing them to compensate motion artifacts or to subtract a background image). The digital images may be of any type (for example, of the 3D type, based on any contrast-specific imaging mode, or even on fundamental B-mode, either alone or in combination), with any size and in any non-zero number (so as to be statistically significant); the intensity values may be of any type (for example, log-compressed values) and coded in any way (for example, color-coded on any number of bits). In any case, the possibility of applying the same method to any representation of the body-part (even not in the form of images) is not excluded. For example, the representation over the non-zero analysis time period of a body-part may be defined by the raw (unprocessed RF) echo signals. In this case, for each selected location the value of said at least one statistical parameter (of the statistical distribution of the response) is obtained by calculating the Hilbert transform of the raw echo signal of the selected location and then the (complex) correlation coefficient or variance thereof, at the level of either its magnitude or phase (with the selected locations that are then segmented as above according to the comparison between the values of these statistical parameter(s) with at least one segmentation threshold).

In an embodiment, said at least one statistical parameter is a plurality of statistical parameters.

However, the statistical parameters may be in any number (down to a single one, or vice-versa three or more).

In an embodiment, the statistical parameters are a central-tendency statistical parameter and a dispersion statistical parameter.

However, it is possible to use any central-tendency statistical parameter (for example, in addition to the (arithmetic) mean and the median, the mode, the geometric mean, the harmonic mean, the truncated mean, the midrange mean, and the like) and/or any dispersion statistical parameter (for example, in addition to the standard deviation, the mean difference, the average deviation, the variance, and the like).

In any case, statistical parameters of different, additional or alternative type may be used (for example, location or shape statistical parameters).

In an embodiment, said step of calculating the value of at least one statistical parameter includes calculating the value of said at least one statistical parameter relating to the response being transformed to provide a transformed statistical distribution of the transformed response over the analysis time period with a skewed shape.

However, this calculation may be implemented in any way according to any transformed statistical distribution (see below). In any case, the possibility of calculating the statistical parameters only from the (original) statistical distribution of the responses is not excluded.

In an embodiment, the transformed statistical distribution is a lognormal statistical distribution.

However, any other transformed statistical distribution with a skewed shape may be used (for example, the gamma or the local density random walk distribution).

In an embodiment, said step of calculating the value of at least one statistical parameter includes calculating the value of at least one further statistical parameter from the statistical distribution of the response over the analysis time period of the selected location, and calculating the value of each statistical parameter by applying a corresponding transformation depending on the transformed statistical distribution to the value of said at least one further statistical parameter.

However, the transformation may be of any type (see below). In any case, nothing prevents transforming the responses and then calculating the desired statistical parameters directly from the transformed responses; for example, it is possible to calculate the lognormal mean and the lognormal standard deviation as:

$$m = \frac{1}{N}\sum_{i=1}^{N} (\ln(X_i)) \quad \text{if } X_i \geq 1$$
$$m = 0 \quad \text{if } X < 1$$

$$s = \sqrt{\frac{1}{N}\sum_{i=1}^{N} (\ln(X_i) - m)^2} \quad \text{if } X_i \geq 1$$
$$s = 0 \quad \text{if } X_i < 1$$

Alternatively, it is also possible to fit each response by a parametric function being an instance of a parametric model representing a distribution function of the transformed statistical distribution (either directly or from a histogram thereof), and then to calculate the desired statistical parameters from this parametric function.

In an embodiment, said step of calculating the value of each statistical parameter by applying a corresponding transformation includes applying a logarithmic transformation to the value of said at least one further statistical parameter.

However, the transformation may be of any type (for example, of the exponential type).

In an embodiment, said at least one statistical parameter is a lognormal mean and a lognormal standard deviation, and said at least one further statistical parameter is a normal mean and a normal median.

However, the statistical parameters and/or the further statistical parameters may be of any type and in any number (for example, as pointed out above).

In an embodiment, said step of calculating the value of each statistical parameter by applying a corresponding transformation includes setting the value of the lognormal mean equal to the natural logarithm of the value of the normal median, and the value of the lognormal standard deviation equal to the square root of twice the natural logarithm of a ratio between the value of the normal mean and the value of the normal median if said ratio is strictly higher than 1 or equal to 0 otherwise.

However, other transformations may be used according to the type of transformed statistical distribution and/or statistical parameters.

In an embodiment, said step of segmenting the selected locations includes segmenting the selected locations according to a comparison between the value of each statistical parameter and a corresponding one of said at least one segmentation threshold.

However, the segmentation thresholds may be defined in any way. For example, it is possible to apply Principal Component Analysis (PCA) techniques to uncorrelate the values of the statistical parameters; moreover, the segmentation thresholds may be calculated from a center of gravity of the values of the corresponding statistical parameters. The selected locations may be segmented according to any comparison between each statistical parameter and the corresponding segmentation threshold (for example, higher or lower in absolute terms or by a predefined percentage, in any combinations). In any case, nothing prevents using a number of segmentation thresholds different from the one of the statistical parameters (for example, when the segmentation is based on any (linear or non-linear) combinations of the statistical parameters).

In an embodiment, said step of segmenting the selected locations includes assigning each selected location of an analysis region of the body-part (comprising a lesion to be analyzed) to a first segment (relating to a hypo-perfused portion of the analysis region) when the value of a central-tendency statistical parameter is higher than the corresponding segmentation threshold and the value of a dispersion statistical parameter is higher than the corresponding segmentation threshold, or to a second segment otherwise; the method further comprises calculating a consolidated value of the responses of the selected locations of the analysis region not comprised in the first segment.

However, this segmentation may be based on other segmentation criteria (for example, high correlation coefficient and low variance of the Hilbert transform of the raw echo signals); moreover, it may be used to calculate any consolidated value of the analysis region (for example, their average time to peak, skewness, and the like).

In an embodiment, said step of segmenting the selected locations includes assigning each selected location of a control region of the body-part (comprising healthy tissue to be compared with the analysis region) to a further first segment (relating to a hyper-perfused portion of the control region) when the value of the central-tendency statistical parameter is lower than the corresponding segmentation threshold and the value of the dispersion statistical parameter is higher than the corresponding segmentation threshold, or to a further second segment otherwise; the method further comprises calculating a further consolidated value of the responses of the selected locations of the control region not comprised in the further first segment.

However, this segmentation may be based on other segmentation criteria (for example, low correlation coefficient and high variance of the Hilbert transform of the raw echo signals); moreover, it may be used to calculate any consolidated value of the control region as above.

In an embodiment, the method further comprises calculating a relative consolidated value of the analysis region with respect to the control region according to a combination of the consolidated value and the further consolidated value.

However, the relative consolidated value may be calculated in any way (for example, as a difference between the consolidated value and the further consolidated value); in any case, the further consolidated value may be used in any other way (for example, for normalizing parameter values of a whole parametric image).

In an embodiment, the contrast agent is a targeted contrast agent capable of circulating within the patient and of being substantially immobilized on a biological target; said step of segmenting the selected locations includes assigning each selected location to a first segment (relating to the immobilized targeted contrast agent) when the value of a central-tendency statistical parameter is higher than the corresponding segmentation threshold and the value of a dispersion statistical parameter is lower than the corresponding segmentation threshold, or to a second segment otherwise.

However, the targeted contrast agent may be of any type (for example, either based on specific or non-specific interactions); moreover, this segmentation may be based on other segmentation criteria (for example, high correlation coefficient and low variance of the Hilbert transform of the raw echo signals).

In any case, the same technique may be used in any other diagnostic imaging application; for example, the same procedure may be re-iterated (once or more times) on a selected segment, or it may be applied repeatedly with different segmentation criteria, with the resulting segmentation masks that are combined by logical operators, such as to obtain the intersection (logic AND), union (logic OR), or exclusive union (XOR) of the corresponding segments.

Generally, similar considerations apply if the same solution is implemented with an equivalent method (by using similar steps with the same functions of more steps or portions thereof, removing some steps being non-essential, or adding further optional steps); moreover, the steps may be performed in a different order, concurrently or in an interleaved way (at least in part).

In any case, it is emphasized that the above-described method is a data-processing (or computational) method that may be implemented independently of any interaction with the patient (and particularly with the contrast agent that may be pre-administered thereto before performing the method). Moreover, the contrast agent may also be administered to the patient in a non-invasive manner (for example, orally for imaging the gastro-intestinal tract or via a nebulizer into the airways), or in any case without any substantial physical intervention thereon that would require professional medical expertise or entail any health risk for the patient (for example, intramuscularly). In any case, although the proposed method may facilitate the task of a physician, it generally only provides intermediate results that may help him/her in analyzing the body-part for example, for diagnostic purposes (even though the diagnosis for curative purposes stricto sensu is always made by the physician himself/herself).

A further embodiment provides a computer program, which is configured for causing a computing system to perform the above-mentioned method when the computer program is executed on the computing system.

A further embodiment provides a computer program product, which comprises a non-transitory computer readable medium embodying a computer program; the computer program is loadable into a working memory of a computing system thereby configuring the computing system to perform the same method.

However, the same solution may be implemented as a stand-alone module, as a plug-in for a control program of the ultrasound scanner, or even directly in the control program itself; it would be readily apparent that it is also possible to deploy the same solution as a service that is accessed through a network (such as in the Internet). In any case, similar considerations apply if the software program (which may be used to implement each embodiment of the present disclosure) is structured in a different way, or if additional modules or functions are provided; likewise, the memory structures may be of other types, or may be replaced with equivalent entities (not necessarily consisting of physical storage media). The program may take any form suitable to be used by any computing (or data-processing) system or in connection therewith (for example, within a virtual machine), thereby configuring the system to perform the desired operations; particularly, the program may be in the form of external or resident software, firmware, or microcode (either in object code or in source code for example, to be compiled or interpreted). Moreover, it is possible to provide the program on any computer-usable medium (and particularly as an article of manufacture on a non-transitory medium); the medium may be any element suitable to contain, store, communicate, propagate, or transfer the program. For example, the medium may be of the electronic, magnetic, optical, electromagnetic, infrared, or semiconductor type; examples of such medium are fixed disks (where the program may be pre-loaded), removable disks, tapes, cards, wires, fibers, wireless connections, networks, broadcast waves, and the like. In any case, the solution according to an embodiment of the present disclosure lends itself to be implemented even with a hardware structure (for example, integrated in a chip of semiconductor material), or with a combination of software and hardware suitably programmed or otherwise configured.

A further embodiment provides a system, which comprises means configured for performing the steps of the above-mentioned method.

However, the same solution may be applied in a system including an ultrasound scanner and a distinct computer (or any equivalent system); in this case, the recorded information is transferred from the ultrasound scanner to the computer for its processing (for example, through a digital, analogue or network connection). In any case, the possibility is not excluded of applying the proposed solution to any other diagnostic imaging system—for example, based on Magnetic Resonance Imaging (MRI) or X-ray Computed Tomography (CT).

Generally, similar considerations apply if the system has a different structure or comprises equivalent components, or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

A further embodiment provides a diagnostic imaging method comprising the following steps. A contrast agent is administered to a patient to cause the contrast agent to perfuse a body-part of the patient. An interrogation signal is applied over a non-zero analysis time period to the body-part. A representation is acquired over the analysis time period of the body-part; the representation comprises, for each location of a set of locations of the body-part, an indication of a response over the analysis time period of the location to the interrogation signal (with the representations that are processed according to the same method as above to segment a set of selected locations comprising all the locations or a part thereof). A condition of the body-part is evaluated according to said segmentation.

However, the method may find application in any kind of diagnostic applications (in the broadest meaning of the term for example, aimed at either discovering new lesions or monitoring known lesions) and for analyzing any kind of body-part (for example, organs, such as liver, prostate or heart, regions or tissues) of any (human or animal) patient. Particularly, the segmentation may be used to identify regions of the body-part in whatever physiological condition for example, discriminating lesions from healthy tissue, or portions of the body-part with different perfusion parameters.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated.

The invention claimed is:

1. A data-processing segmentation method for use in diagnostic imaging applications, the method comprising:
    providing a representation over a non-zero analysis time period of a body-part being perfused with a contrast agent, the representation comprising, for each location of a set of locations of the body-part, an indication of a response over the analysis time period of the location to an interrogation signal;
    calculating, for each selected location of a set of selected locations, the value of at least one statistical parameter of a statistical distribution of the response over the analysis time period of the selected location, the set of selected locations comprising all the locations or a part thereof; and
    segmenting the selected locations according to a comparison between the values of said at least one statistical parameter for the selected locations with at least one segmentation threshold.

2. The method according to claim 1, wherein said providing a representation over a non-zero analysis time period of a body-part includes:
    providing a sequence of digital images of the body-part registered during the analysis time period, each digital image comprising an intensity value for each location based on the response of the location at a corresponding acquisition instant in the analysis time period;
    and wherein said calculating the value of at least one statistical parameter includes:
    calculating the value of said at least one statistical parameter from the intensity values of the selected location along the digital images.

3. The method according to claim 1, wherein said at least one statistical parameter is a plurality of statistical parameters.

4. The method according to claim 3, wherein the statistical parameters are a central-tendency statistical parameter and a dispersion statistical parameter.

5. The method according to claim 1, wherein said calculating the value of at least one statistical parameter includes:
    calculating the value of said at least one statistical parameter relating to the response being transformed to provide a transformed statistical distribution of the transformed response over the analysis time period with a skewed shape.

6. The method according to claim 5, wherein the transformed statistical distribution is a lognormal statistical distribution.

7. The method according to claim 5, wherein said calculating the value of at least one statistical parameter includes:
    calculating the value of at least one further statistical parameter from the statistical distribution of the response over the analysis time period of the selected location; and
    calculating the value of each statistical parameter by applying a corresponding transformation depending on the transformed statistical distribution to the value of said at least one further statistical parameter.

8. The method according to claim 7, wherein said calculating the value of each statistical parameter by applying a corresponding transformation includes:
    applying a logarithmic transformation to the value of said at least one further statistical parameter.

9. The method according to claim 7, wherein said at least one statistical parameter is a lognormal mean and a lognormal standard deviation, and said at least one further statistical parameter is a normal mean and a normal median.

10. The method according to claim 9, wherein said calculating the value of each statistical parameter by applying a corresponding transformation includes:
    setting the value of the lognormal mean equal to the natural logarithm of the value of the normal median, and the value of the lognormal standard deviation equal to the square root of twice the natural logarithm of a ratio between the value of the normal mean and the value of the normal median if said ratio is strictly higher than 1 or equal to 0 otherwise.

11. The method according to claim 1, wherein said segmenting the selected locations includes:
    segmenting the selected locations according to a comparison between the value of each statistical parameter and a corresponding one of said at least one segmentation threshold.

12. The method according to claim 11, wherein said segmenting the selected locations includes:
    assigning each selected location of an analysis region of the body-part comprising a lesion to be analyzed to a first segment relating to a hypo-perfused portion of the analysis region when the value of a central-tendency statistical parameter is higher than the corresponding segmentation threshold and the value of a dispersion statistical parameter is higher than the corresponding segmentation threshold, or to a second segment otherwise;
    the method further comprising:
    calculating a consolidated value of the responses of the selected locations of the analysis region not comprised in the first segment.

13. The method according to claim 12, wherein said segmenting the selected locations includes:
    assigning each selected location of a control region of the body-part comprising healthy tissue to be compared with the analysis region to a further first segment relating to a hyper-perfused portion of the control region when the value of the central-tendency statistical parameter is lower than the corresponding segmentation threshold and the value of the dispersion statistical parameter is higher than the corresponding segmentation threshold, or to a further second segment otherwise;

the method further comprising:

calculating a further consolidated value of the responses of the selected locations of the control region not comprised in the further first segment.

14. The method according to claim 13, further comprising:

calculating a relative consolidated value of the analysis region with respect to the control region according to a combination of the consolidated value and the further consolidated value.

15. The method according to claim 11, wherein the contrast agent is a targeted contrast agent capable of circulating within the patient and of being substantially immobilized on a biological target, said segmenting the selected locations including:

assigning each selected location to a first segment relating to the immobilized targeted contrast agent when the value of a central-tendency statistical parameter is higher than the corresponding segmentation threshold and the value of a dispersion statistical parameter is lower than the corresponding segmentation threshold, or to a second segment otherwise.

16. A computer program product comprising a non-transitory computer-readable medium embodying a computer program, the computer program being loadable into a working memory of a computing system thereby configuring the computing system:

to provide a representation over a non-zero analysis time period of a body-part being perfused with a contrast agent, the representation comprising, for each location of a set of locations of the body-part, an indication of a response over the analysis time period of the location to an interrogation signal;

to calculate, for each selected location of a set of selected locations, the value of at least one statistical parameter of a statistical distribution of the response over the analysis time period of the selected location, the set of selected locations comprising all the locations or a part thereof; and to segment the selected locations according to a comparison between the values of said at least one statistical parameter for the selected locations with at least one segmentation threshold.

17. A system for use in diagnostic imaging applications, the system comprising:

means for providing a representation over a non-zero analysis time period of a body-part being perfused with a contrast agent, the representation comprising, for each location of a set of locations of the body-part, an indication of a response over the analysis time period of the location to an interrogation signal;

means for calculating, for each selected location of a set of selected locations, the value of at least one statistical parameter of a statistical distribution of the response over the analysis time period of the selected location, the set of selected locations comprising all the locations or a part thereof; and means for segmenting the selected locations according to a comparison between the values of said at least one statistical parameter for the selected locations with at least one segmentation threshold.

18. The system according to claim 17, wherein the means for providing a representation over a non-zero analysis time period of a body-part includes:

means for providing a sequence of digital images of the body-part registered during the analysis time period, each digital image comprising an intensity value for each location based on the response of the location at a corresponding acquisition instant in the analysis time period;

and wherein the means for calculating the value of at least one statistical parameter includes:

means for calculating the value of said at least one statistical parameter from the intensity values of the selected location along the digital images.

19. The system according to claim 17, wherein said at least one statistical parameter is a plurality of statistical parameters.

20. The system according to claim 19, wherein the statistical parameters are a central-tendency statistical parameter and a dispersion statistical parameter.

21. The system according to claim 17, wherein the means for calculating the value of at least one statistical parameter includes:

means for calculating the value of said at least one statistical parameter relating to the response being transformed to provide a transformed statistical distribution of the transformed response over the analysis time period with a skewed shape.

22. The system according to claim 21, wherein the transformed statistical distribution is a lognormal statistical distribution.

23. The system according to claim 21, wherein the means for calculating the value of at least one statistical parameter includes:

means for calculating the value of at least one further statistical parameter from the statistical distribution of the response over the analysis time period of the selected location; and means for calculating the value of each statistical parameter by applying a corresponding transformation depending on the transformed statistical distribution to the value of said at least one further statistical parameter.

24. The system according to claim 23, wherein the means for calculating the value of each statistical parameter by applying a corresponding transformation includes:

means for applying a logarithmic transformation to the value of said at least one further statistical parameter.

25. The system according to claim 23, wherein said at least one statistical parameter is a lognormal mean and a lognormal standard deviation, and said at least one further statistical parameter is a normal mean and a normal median.

26. The system according to claim 25, wherein the means for calculating the value of each statistical parameter by applying a corresponding transformation includes:

means for setting the value of the lognormal mean equal to the natural logarithm of the value of the normal median, and the value of the lognormal standard deviation equal to the square root of twice the natural logarithm of a ratio between the value of the normal mean and the value of the normal median if said ratio is strictly higher than 1 or equal to 0 otherwise.

27. The system according to claim 17, wherein the means for segmenting the selected locations includes:

means for segmenting the selected locations according to a comparison between the value of each statistical parameter and a corresponding one of said at least one segmentation threshold.

28. The system according to claim 27, wherein the means for segmenting the selected locations includes:

means for assigning each selected location of an analysis region of the body-part comprising a lesion to be analyzed to a first segment relating to a hypo-perfused portion of the analysis region when the value of a central-tendency statistical parameter is higher than the corresponding segmentation threshold and the value of a dispersion statistical parameter is higher than the corresponding segmentation threshold, or to a second segment otherwise;

the system further comprising:

means for calculating a consolidated value of the responses of the selected locations of the analysis region not comprised in the first segment.

29. The system according to claim 28, wherein the means for segmenting the selected locations includes:

means for assigning each selected location of a control region of the body-part comprising healthy tissue to be compared with the analysis region to a further first segment relating to a hyper-perfused portion of the control region when the value of the central-tendency statistical parameter is lower than the corresponding segmentation threshold and the value of the dispersion statistical parameter is higher than the corresponding segmentation threshold, or to a further second segment otherwise;

the system further comprising:

means for calculating a further consolidated value of the responses of the selected locations of the control region not comprised in the further first segment.

30. The system according to claim 29, further comprising:

means for calculating a relative consolidated value of the analysis region with respect to the control region according to a combination of the consolidated value and the further consolidated value.

31. The system according to claim 27, wherein the contrast agent is a targeted contrast agent capable of circulating within the patient and of being substantially immobilized on a biological target, the means for segmenting the selected locations including:

means for assigning each selected location to a first segment relating to the immobilized targeted contrast agent when the value of a central-tendency statistical parameter is higher than the corresponding segmentation threshold and the value of a dispersion statistical parameter is lower than the corresponding segmentation threshold, or to a second segment otherwise.

32. A diagnostic method comprising:

administering a contrast agent to a patient to cause the contrast agent to perfuse a body-part of the patient;

applying an interrogation signal over a non-zero analysis time period to the body-part;

acquiring a representation over the analysis time period of the body-part, wherein the representation comprises, for each location of a set of locations of the body-part, an indication of a response over the analysis time period of the location to the interrogation signal, the representations being processed according to the method of claim 1 to segment a set of selected locations comprising all the locations or a part thereof; and evaluating a condition of the body-part according to said segmentation.

* * * * *